(12) United States Patent
Saito et al.

(10) Patent No.: US 7,787,122 B2
(45) Date of Patent: Aug. 31, 2010

(54) OPTICAL WAVEFORM MEASUREMENT DEVICE AND MEASUREMENT METHOD THEREOF, COMPLEX REFRACTIVE INDEX MEASUREMENT DEVICE AND MEASUREMENT METHOD THEREOF, AND COMPUTER PROGRAM RECORDING MEDIUM CONTAINING THE PROGRAM

(75) Inventors: Shingo Saito, Tokyo (JP); Masaru Iida, Tokyo (JP); Masaaki Ashida, Tokyo (JP)

(73) Assignee: National Institute of Information and Communications Technology, Tokyo (JP)

( * ) Notice: Subject to any disclaimer, the term of this patent is extended or adjusted under 35 U.S.C. 154(b) by 661 days.

(21) Appl. No.: 10/561,280

(22) PCT Filed: Jun. 18, 2004

(86) PCT No.: PCT/JP2004/008609

§ 371 (c)(1),
(2), (4) Date: Mar. 19, 2007

(87) PCT Pub. No.: WO2004/113885

PCT Pub. Date: Dec. 29, 2004

(65) Prior Publication Data

US 2007/0273357 A1 Nov. 29, 2007

(51) Int. Cl.
*G01N 21/00* (2006.01)
(52) U.S. Cl. .................................................. 356/432
(58) Field of Classification Search ........................ None
See application file for complete search history.

(56) References Cited

U.S. PATENT DOCUMENTS 5,952,818 A 9/1999 Zhang et al.

6,111,416 A 8/2000 Zhang et al.
6,476,596 B1 * 11/2002 Wraback et al. ......... 324/158.1

(Continued)

FOREIGN PATENT DOCUMENTS

JP 8-320254 A 12/1996

(Continued)

OTHER PUBLICATIONS

Kono, S., Tani, M., and Sakai ,K.,"Coherent Detection of Mid-infrared Radiation up to 60THz with an LT-GaAs Photoconductive Antenna", IEE Proceedings-Optoelectronics, Jun. 2002, pp. 105 to 109.

(Continued)

*Primary Examiner*—Tu T Nguyen
(74) *Attorney, Agent, or Firm*—Sampson & Associates, P.C.

(57) ABSTRACT

A light-waveform measuring device and method include a complex-refractive-index measuring device and a computer-program recording medium An electric field of an electromagnetic wave, in a light region having wavelengths smaller than those of electromagnetic waves in a near-infrared region, is measured, and time-varying waveforms are outputted. Gate-pulse-light generating means, measurement-light generating means and light-detecting means for detecting measurement light, are included, The measurement light is coherent light having a wavelength smaller than those of a near-infrared region. The gate pulse light is coherent light with a pulse width smaller than a period of the measurement light. A physical quantity, based on carriers generated from the measurement light and the gate pulse light is measured.

24 Claims, 18 Drawing Sheets

FIRST EMBODIMENT OF THE INVENTION

U.S. PATENT DOCUMENTS 6,529,281 B2 *   3/2003   Takeshita et al. ............ 356/614

FOREIGN PATENT DOCUMENTS

JP          2002-277393 A       9/2002

OTHER PUBLICATIONS

Tani, Masahiko, Kono, Shunsuke, Nakajima, Makoto, Iida, Masaru and Sakai, Kiyomi, "Generation and Detection of Ultrabroadband Terahertz Radiation with Photoconductive Antennas", Conference Digest.,Twenty Seventh International Conference on Infrared and Millimeter Waves, Sep. 2002, pp. 125 to 126.

Duvillaret, L., Garet, Frederic, and Coutaz, Jean-Louis,"A Reliable Method for Extraction of Material Parameters in Terahertz Time-Domain Spectroscopy", IEEE Journal of Selected Topics in Quantum Electronics, vol. 2, No. 3, Sep. 1996, pp. 739 to 746.

Sun, F. G., and Jiang, Zhiping; Zhang, X.-C., Aalysis of Terahertz Pulse Measurement with a Chirped Probe Beam, Applied Physics Letters, vol. 73, No. 16, Oct. 19, 1998, pp. 2233 to 2235.

Shan, Jie, Weling, Aniruddha S., Knoesel, Ernst,Bartels, Ludwig, Bonn, Mischa, Nahata, Ajay, Reider, George A., Heinz, Tony F., "Single-shot Measurement of Terahertz Electromagnetic Pulses by Use of Electro-optic Sampling", Optics Letters, vol. 25, No. 6, Mar. 15, 2000, pp. 426 to 428.

* cited by examiner

Fig. 2
EMBODIMENT OF DETECTOR OF THE INVENTION
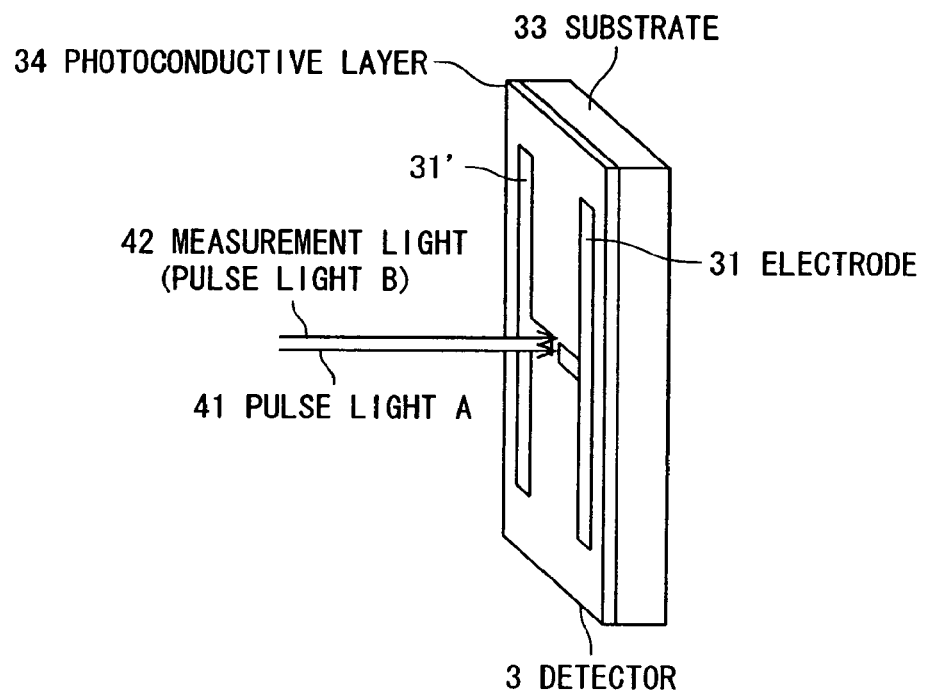
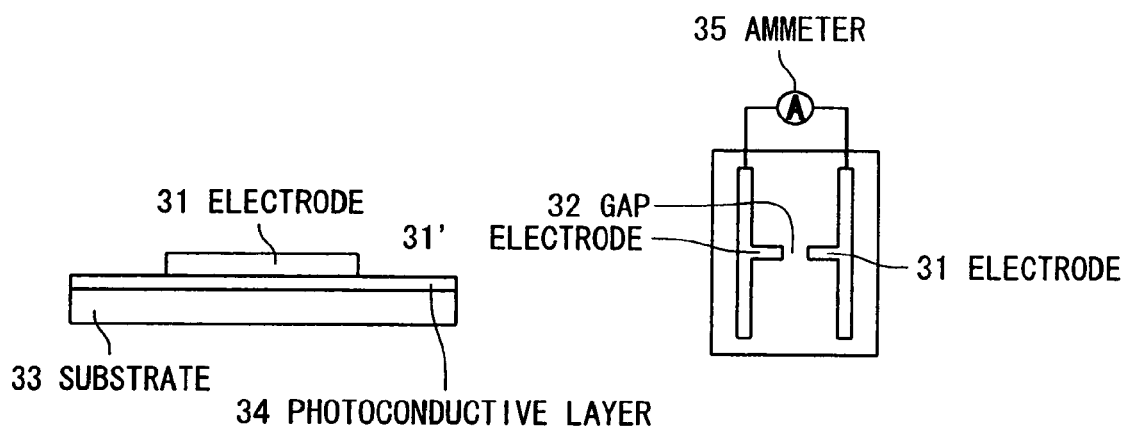

Fig. 3
EXPLANATION VIEW OF PULSE WIDTH OF GATE PULSE LIGHT FOR REALIZING T
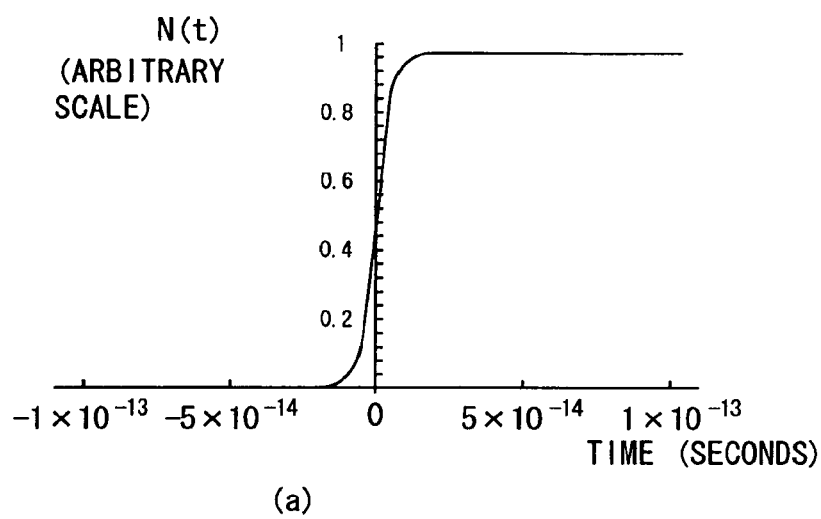
(a)
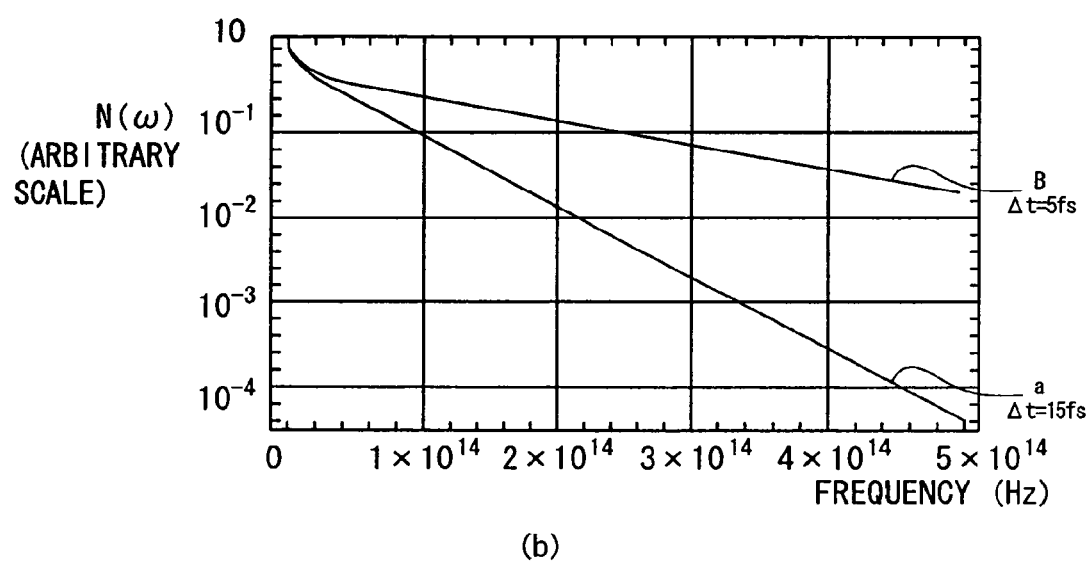
(b)

Fig. 7
FLOW CHART IN DATA PROCESSING DEVICE ACCORDING TO SECOND EMBODIMENT OF THE INVENTION
(a)
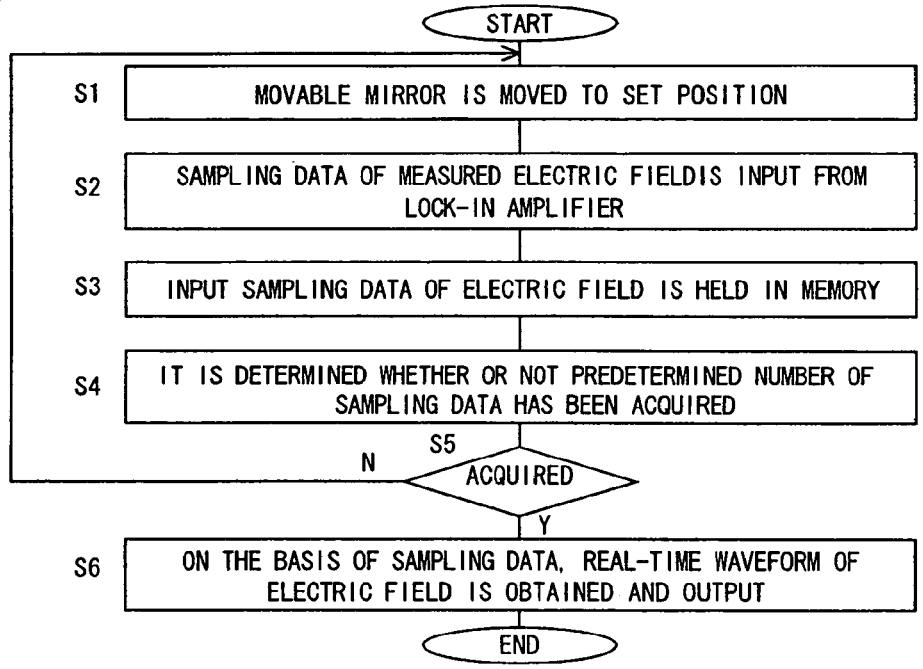
(b)
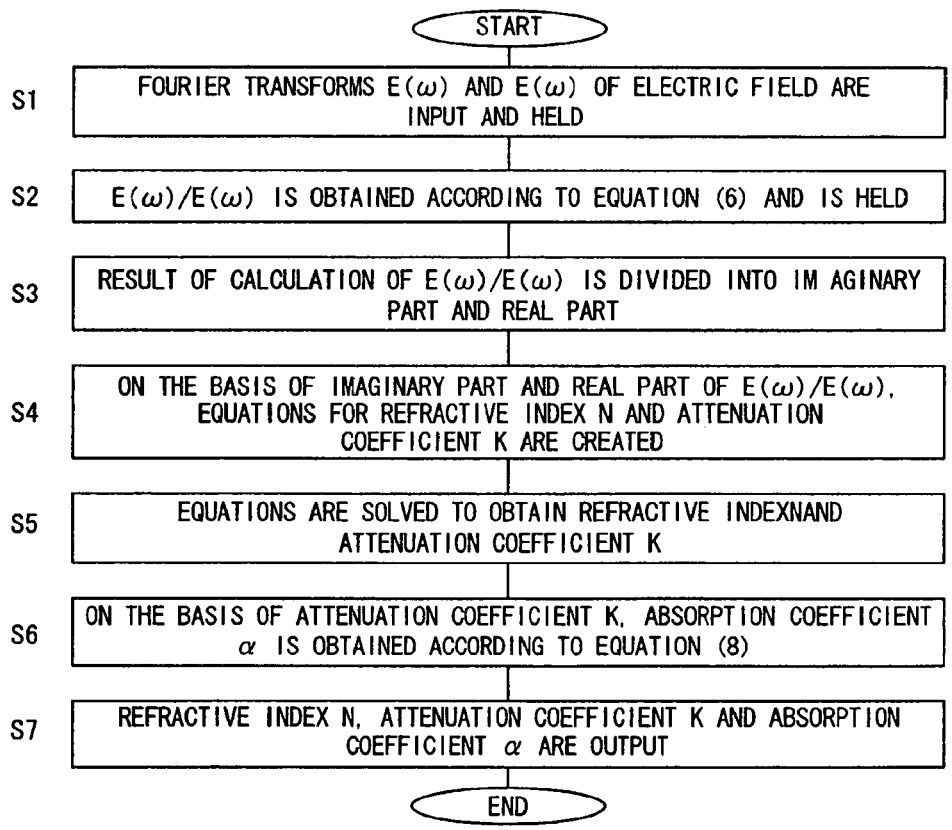

Fig. 9
FOURTH EMBODIMENT OF THE INVENTION
FIRST METHOD FOR PERFORMING MEASUREMENT FOR PLURAL OPTICAL-PATH
DIFFERENCES THROUGH SINGLE IRRADIATION OF GATE PULSE LIGHT
(a)
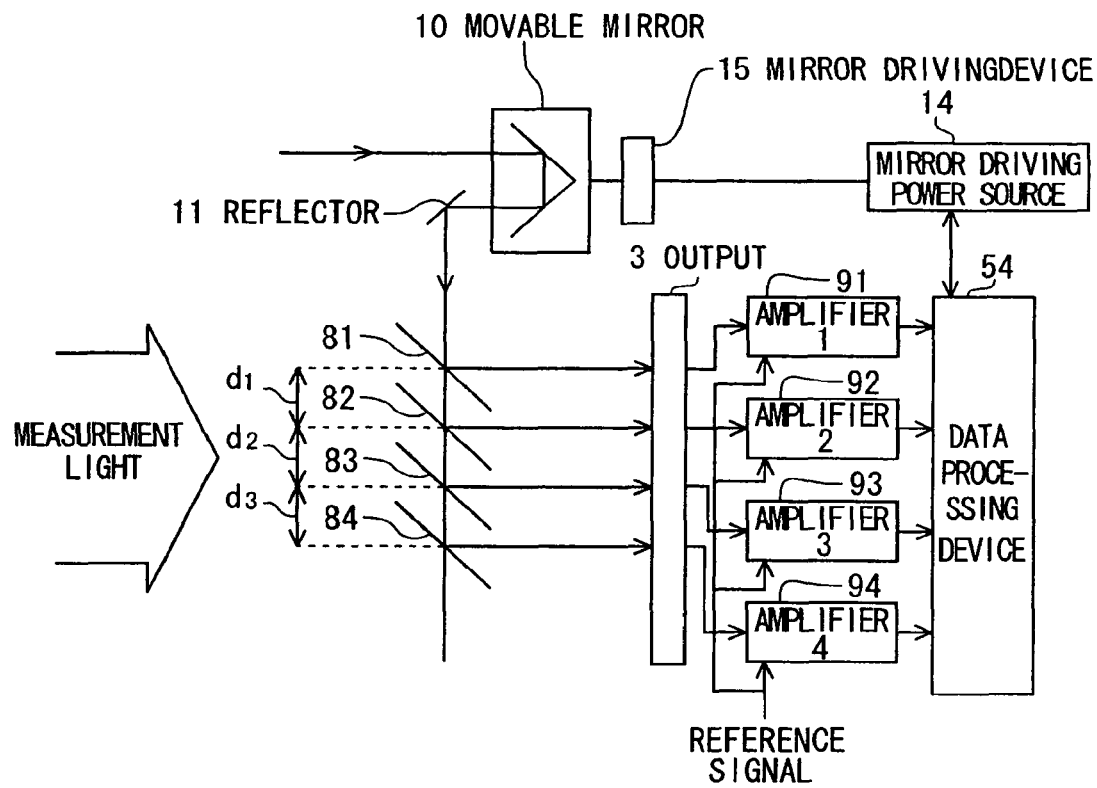
(b)
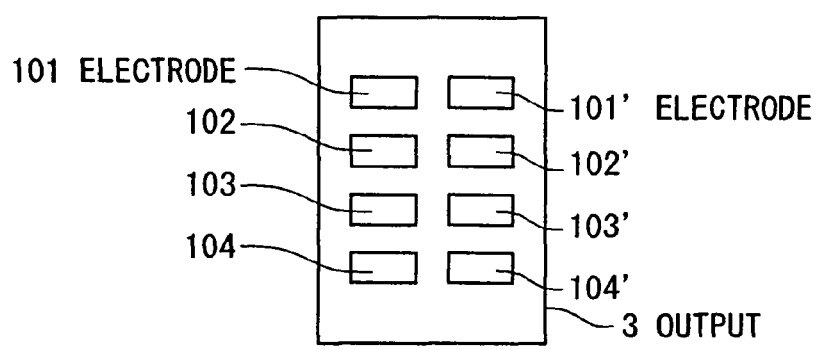

Fig. 11
FOURTH EMBODIMENT
(SECOND METHOD FOR PERFORMING MEASUREMENT FOR PLURAL OPTICAL-PATH DIFFERENCES THROUGH SINGLE IRRADIATION OF GATE PULSE)
(a)
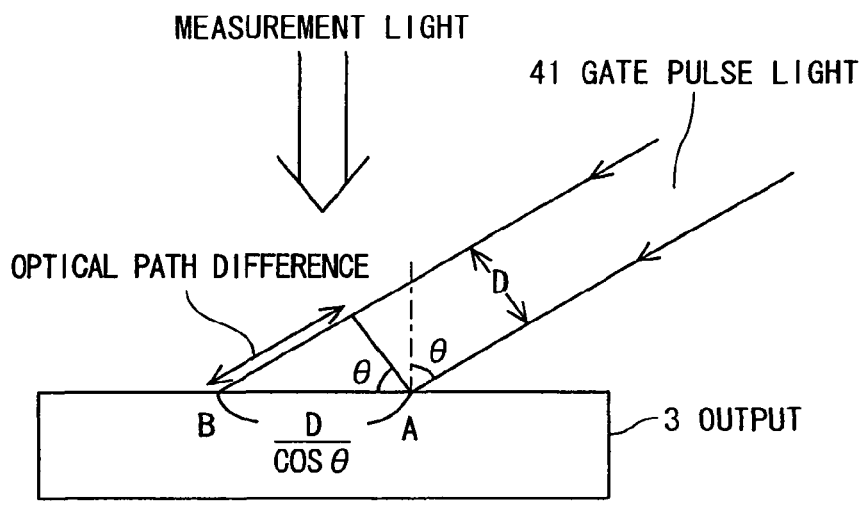
(b)
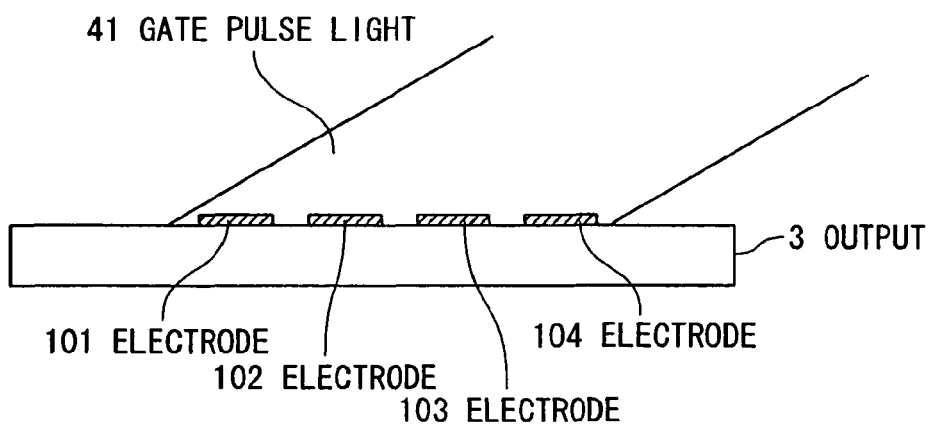

FLOW CHART IN DATA PROCESSING DEVICE ACCORDING TO FOURTH EMBODIMENT
OF THE INVENTION

OPTICAL WAVEFORM MEASUREMENT DEVICE AND MEASUREMENT METHOD THEREOF, COMPLEX REFRACTIVE INDEX MEASUREMENT DEVICE AND MEASUREMENT METHOD THEREOF, AND COMPUTER PROGRAM RECORDING MEDIUM CONTAINING THE PROGRAM

TECHNICAL FIELD

The present invention relates to a light-waveform measuring device and its measuring method, a complex-refractive-index measuring device and its measuring method, and a computer-program recording medium having programs for the same stored therein. More particularly, the present invention relates to devices and methods for measuring, in real time, a waveform of an electric field of an electromagnetic wave with a wavelength smaller than those of terahertz electromagnetic waves, and more particularly, for measuring an electric field of light with a wavelength smaller than those of light in a near-infrared region. Further, the present invention relates to a complex-refractive-index measuring device for measuring an electric field of light and measuring a complex refractive index of a sample on the basis of the result of measurement. Further, the present invention relates to a computer-program recording medium having stored therein programs for obtaining the complex refractive index of the sample, on the basis of data of the waveform of the electric field.

BACKGROUND ART

Conventionally, it has been impossible to observe time-varying electric field waveforms of electromagnetic waves in a light region having wavelengths smaller than those of electromagnetic waves in a near-infrared region, and it has been possible to measure only the intensities thereof. Further, measurements of a refractive index and an absorption coefficient of a material with respect to light have been conducted using ellipsometry.

As previously described, in the light regions having wavelengths smaller than those of electromagnetic waves in the near-infrared region, only the time-varying intensities have been measured. However, it has been impossible to observe the waveforms indicating the time-varying electric fields.

Further, conventional measurements for the refractive indexes and the absorption coefficients of materials utilizing ellipsometry have involve sweeping of the wavelength and rotating of a polarizer, thereby requiring a long time for measurements and complex operations.

DISCLOSURE OF THE INVENTION

It is an object of the present invention to measure an electric field of an electromagnetic wave in a light region having a wavelength smaller than those of electromagnetic waves in a near-infrared region and output a time-varying waveform thereof. It is also an object of the present invention to enable easily measuring a complex refractive index, on the basis of the result of measurement of an electric-field waveform of a terahertz electromagnetic wave or an electromagnetic wave in a light region having a wavelength smaller than that of a terahertz electromagnetic wave.

Means for Solving the Problem

FIG. 18 illustrates an example of conventional measurement of a waveform of an electric field of a terahertz electromagnetic wave. The solid line represents the result of measurement of a terahertz electromagnetic wave which does not pass through a sample while the dot line represents the result of measurement of the terahertz electromagnetic wave passed through the sample. FIG. 18 illustrates the waveform of the electric field of the terahertz electromagnetic wave, which is the real-time change. By obtaining the electric-field waveforms of the measurement light which does not pass through a sample and the measurement light having passed through the sample with respect to an electromagnetic wave in the light region, a complex refractive index of a material can be obtained on the basis of the change of the waveforms. Further, on the basis of the complex refractive index, a refractive index $n$ and an absorption coefficient $\alpha$ of the material can be obtained.

FIG. 18 illustrates the waveforms of a terahertz electromagnetic wave having a great wavelength. However, the present invention enables observation of the waveforms of electromagnetic waves in a light region having smaller wavelengths than those of a near-infrared region. Further, the present invention enables determination of the complex refractive index, the refractive index and the absorption coefficient of a material with respect to light, on the basis of the result of measurement of the waveform indicating the time-varying electric field (hereinafter, simply referred to as the electric-field waveform) of a terahertz electromagnetic wave or an electromagnetic wave in a light-wavelength region having a smaller wavelength than that of the electromagnetic wave.

A light-waveform measuring device according to the present invention includes gate-pulse-light generating means, measurement-light generating means, and light-detecting means for detecting measurement light, wherein gate pulse light is coherent pulse light having a pulse width smaller than a wavelength of measurement light, the measurement light is coherent light having a wavelength smaller than those of a near-infrared region. Accordingly, the light-waveform measuring device according to the present invention directs the gate pulse light and the measurement light to the light-detecting means to generate carriers therein, measures a physical quantity (electric current, voltage or the like) based on the carriers, measures an electric field of the measurement light and outputs a waveform of the electric field of the measurement light. The measurement light may be light with a frequency of 10 GHz to 67 THz.

A light-waveform measuring device according to the present invention includes gate-pulse-light generating means, measurement-light generating means, and light-detecting means for detecting measurement light, both of gate pulse light and measurement light being coherent lights, the measurement light being a coherent electromagnetic wave or coherent visible light having a wavelength smaller than those of terahertz electromagnetic waves, the gate pulse light being directed to the light-detecting means to generate carriers therein, a physical quantity based on the carriers being measured, and an electric field of the measurement light being measured on the basis of the physical quantity, wherein plural pairs of electrodes are provided, there are provided different optical-path differences for the gate pulse light directed to the gaps between the respective pairs of electrodes, and the physical quantities generated in the respective gaps between the electrodes are acquired as sampling data, with the plural optical-path differences and with a single irradiation of the gate pulse light to measure the electric field of the measurement light.

A light-waveform measuring device according to the present invention includes gate-pulse-light generating means, measurement-light generating means, and light-detecting means for detecting measurement light, wherein both of gate pulse light and measurement light are coherent lights, the measurement light is coherent light having a wavelength smaller than those of a near-infrared region, the gate pulse light has a pulse width smaller than a period of the measurement light, the measurement light and the gate pulse light are directed to the light-detecting means to generate carriers therein, a physical quantity based on the carriers is measured, and an electric field of the measurement light is measured, in real time, on the basis of the physical quantity.

A light-waveform measuring method according to the present invention includes gate-pulse-light generating means, measurement-light generating means, and light-detecting means for detecting measurement light, both of gate pulse light and measurement light being coherent lights, the measurement light being a coherent electromagnetic wave or coherent visible light having a wavelength smaller than those of terahertz electromagnetic waves, the gate pulse light being directed to the light-detecting means to generate carriers therein, a physical quantity based on the carriers is measured, and an electric field of the measurement light is measured on the basis of the physical quantity, wherein the light-detecting means includes plural pairs of electrodes, there are provided different optical-path differences for the gate pulse light directed to the gaps between the respective pairs of electrodes, and the physical quantities generated in the respective gaps between the electrodes are acquired as sampling data, with the plural optical-path differences and with a single irradiation of the gate pulse light to measure the electric field of the measurement light.

A complex-refractive-index measuring device according to the present invention includes gate-pulse-light generating means, measurement-light generating means, light-detecting means for detecting measurement light, and data processing means. In addition, both of gate pulse light and measurement light are coherent lights, the gate pulse light is directed to the light-detecting means to generate carriers therein, a physical quantity (electric current, voltage or the like) based on the carriers is measured, and an electric field of the measurement light is measured on the basis of the physical quantity. Further, the device includes means for holding measurement data. Electric fields of a measurement light which does not pass through a sample and the measurement light having passed through the sample are measured in real time, an amplitude change and a phase change are obtained, and on the basis of the changes, a complex refractive index of the sample is measured. Further, on the basis of the complex refractive index, a refractive index n and an absorption coefficient α of the sample are obtained through a single measurement.

A complex-refractive-index measuring method according to the present invention includes gate-pulse-light generating means, measurement-light generating means, light-detecting means for detecting measurement light, and data processing means, both of gate pulse light and measurement light being coherent lights, the gate pulse light having a pulse width smaller than a period of the measurement light, the gate pulse light being directed to the light-detecting means to generate carriers therein, a physical quantity based on the carriers being measured, and an electric field of the measurement light being measured on the basis of the physical quantity, wherein the data processing means includes a data holding unit for holding the measurement data, and holds measurement data of an electric field of the measurement light which does not pass through a sample and an electric field of the measurement light having passed through the sample, and makes a comparison between the electric field of the measurement light which does not pass through the sample and the electric field of the measurement light having passed through the sample to obtain the complex refractive index of the sample. The measurement light may be light with a frequency of 10 GHz to 67 THz.

A computer-program recording medium according to the present invention includes: a program for inputting data obtained by applying a Fourier transform to measurement data of an electric field of a waveform of measurement light; and a program for obtaining a complex refractive index on the basis of the Fourier transforms of the measurement light which does not pass through a sample and the measurement light which has passed through the sample, wherein the complex refractive index of the sample is obtained by a computer, on the basis of the measurement data of the electric-field waveform of the measurement light.

Effects of the Invention

According to the present invention, it is possible to easily observe a waveform of an electric field of an electromagnetic wave in a light region having a wavelength smaller than those of a near-infrared region. This enables easily and accurately measuring a complex refractive index, a refractive index and an absorption coefficient of a sample with respect to light.

Further, when plural electrodes are placed on a detector, it is possible to determine plural sampling data of an electric field of measurement light at different phases of a waveform, within a single measurement period, through a single irradiation of gate pulse light.

Furthermore, it is possible to easily obtain a complex refractive index, a refractive index and an absorption coefficient at respective points within a plain of a sample, thereby enabling easily determining the uniformity of the sample within the plain. Even when the measurement light can not transmit through the sample, it is possible to easily obtain the complex refractive index thereof.

BRIEF DESCRIPTION OF THE DRAWINGS

FIG. 2 is a diagram illustrating a detector according to an embodiment of the present invention.

FIG. 3 is an explanation view of a pulse width of gate pulse light for realizing the present invention.

FIG. 7 is a flow chart executed in the data processing device according to the second embodiment of the present invention.

FIG. 9 is a diagram illustrating a first method for performing measurement for plural optical-path differences through a single irradiation of gate pulse light, according to a fourth embodiment of the present invention.

FIG. 11 is a diagram illustrating a second method for performing measurement for plural optical-path differences through a single irradiation of gate pulse light, according to the fourth embodiment of the present invention.

EXPLANATION OF REFERENCE NUMERALS

1: pulse light source, 2: measurement light source, 3: detector, 4: measuring device, 10: movable mirror, 11: reflector, 12: semi-transparent mirror, 14: mirror driving power source, 15: mirror driving device

BEST MODE FOR CARRYING OUT THE INVENTION

Figure 1:
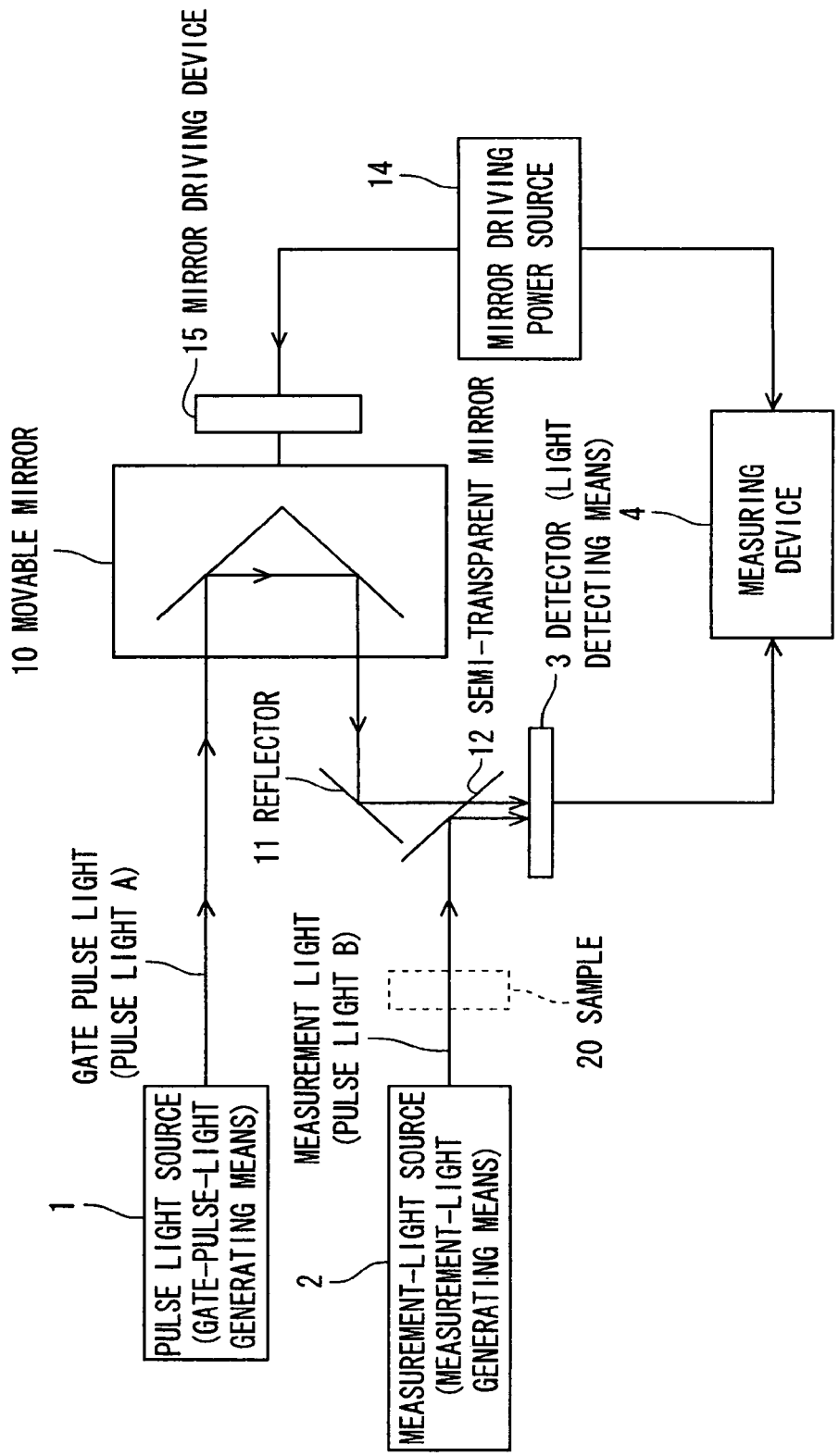
FIG. 1 is a diagram illustrating a first embodiment of the present invention.

FIG. 1 is a light waveform measuring device and a complex-refractive-index measuring device according to a first embodiment of the present invention, illustrating a basic embodiment of the present invention. In FIG. 1, 1 is a pulse light source which is gate-pulse-light generating means. The pulse light source 1 generates gate pulse light and generates coherent light with a coherence characteristic (hereinafter, referred to as coherence light). The gate pulse light generated from the pulse light source 1 is referred to as pulse light A. For example, it is pulse light having a wavelength within the range of 500 to 800 nm and a pulse width of 10 fs. The pulse light source can generate pulses with a wavelength within the range of 700 to 950 nm and a pulse width of about 5 fs with a chirp compensation mirror. Further, the pulse light source can generate pulses with a wavelength within the range of 450 to 700 nm and a pulse width of 4 fs or less and also can generate pulses with a wavelength within the range of 700 to 1600 nm and a pulse width of 10 fs or less, with a non-collinear optical parametric amplifier (NOPA). Also, it can obtain laser pulses with a pulse width of 1 fs or less in a soft X-ray region, which are usable. 2 is a measurement-light source which is measurement-light generating means. The measurement-light source 2 generates coherent measurement light. The measurement light is continuous-wave laser light or coherent light having correlation to the pulse light A from the pulse light source 1. When the measurement light is pulse light, the pulse light is referred to as pulse light B. The pulse Light B is coherent light with a wavelength within the range of 1.2 to 10 μm, and for example, 2 μm and a pulse width of 200 fs, for example.

3 is a detector which is light detecting means. When the detector 3 is irradiated with the pulse light A, the detector 3 generates carriers with the pulse light A. The detector 3 is irradiated with the measurement light generated from the measurement light source 2, and carriers are generated therein by the pulse light A as the gate light. The carriers generate a physical quantity (an electric current, a voltage or the like) in response to the electric field of the measurement light and the physical quantity is measured. Then, the physical quantity is detected as sampling data of the electric-field waveform of the measurement light. 4 is a measuring device which measures the electric field of the measurement light detected by the detector 3.

10 is a movable mirror for continuously varying an optical path length of the pulse light A. 11 is a reflector. 12 is a semi-transparent mirror. 15 is a mirror driving device which is for moving the movable mirror 10. 14 is a mirror driving power source for the movable mirror 10. 20 is a sample whose complex refractive index is to be measured.

In the configuration of FIG. 1, the measurement light generated from the measurement light source 2 is reflected by the semi-transparent mirror 12, and is directed to the detector 3. The pulse light A which is gate pulse light generated from the pulse light source 1 is reflected by the movable mirror 10 and the reflector 11, transmitted through the semi-transparent mirror 12 and is directed to the detector 3. The irradiation of the pulse light A causes carriers in the detector 3 and the carriers generate an electric current depending on the magnitude of the electric field of the measurement light. The electric current is detected by the measuring device 4. By continuously moving the movable mirror 10 through the mirror driving power source 14 and the mirror driving device 15 for continuously changing the optical path length of the pulse light A from the pulse light source 1 to the detector 3, it is possible to continuously measure the electric field of the measurement light which is sampled with the pulse light A as gate pulse light. In the case where the present invention is used as a light waveform determination device, the measuring device 4 observes and outputs the waveform of the measurement light. Also, in the case of using the device according to the present invention as a complex-refractive-index determination device, the amplitude change and the phase change are obtained on the basis of the waveform of the measurement light which does not pass through the sample and the waveform of the measurement light which does not pass therethrough, and then, a complex refractive index p of the sample is obtained therefrom. Further, on the basis of the complex refractive index, a refractive index n, an attenuation coefficient k and an absorption coefficient α are obtained.

FIG. 2(a) illustrates an example of a detector for use in the present invention. In FIG. 2(a), 3 is a detector. 31 and 31' are electrodes. 33 is a substrate. 34 is a photoconductive layer. 41 is pulse light A to be directed to a gap 32 between the electrodes 31 and 31'. 42 is measurement light.

FIG. 2(b) is a cross-sectional view of the detector. 33 is a substrate which is made of, for example, a semi-insulating GaAs. 34 is a photoconductive layer which is made of, for example, GaAs grown at a low temperature. Also, the photoconductive layer may be made of GaSb, a low-temperature grown GaSb, InAs or the like. Alternatively, the photoconductive layer may be formed by depositing an oxide such as a copper oxide (for example, $Sr_2CuO_3$, $SrCuO_2$, $SrCuO_2Cl_2$, or the like) on another substrate. 31 is an electrode made of, for example, Au. FIG. 2(c) is a plan view of the detector 3. 3 is the detector. 31 and 31' are the electrodes. 32 is the gap having an interval of about 5 μm or less. 35 is an ammeter.

In FIG. 2(a), when the pulse light A with a time width smaller than the wavelength of the measurement light is directed in a state where the detector 3 is irradiated with the measurement light, the irradiation of the pulse light A causes carriers in the photoconductive layer 34, thus causing an electric current depending on the magnitude of the electric field of the pulse light B to flow through the electrodes 31 and 31'. By measuring the electric current, it is possible to measure the electric field of the measurement light which is sampled with the pulse light A as the gate pulse light. By continuously changing the time at which the pulse light A is directed, it is possible to observe the change (waveform) of the electric field of the measurement light with time.

In FIGS. 2(a), 2(b) and 2(c), the detected electric current j at a time t can be expressed as follows, wherein the amplitude of the measurement light at the time t is E(t) and the concentration of carriers generated in the substrate by the pulse light A is N(t).

[Equation 1]

$$j(t) \propto \int E(\tau)N(\tau-t)d\tau \quad (1)$$

FIGS. 3(a) and 3(b) illustrate the result of evaluations of the pulse width of the gate pulse light required for realizing the present invention. FIG. 3(a) illustrates an example of the change of the concentration of carrier generated by the pulse light A with time. The horizontal axis represents the time (seconds). The relationship between the carrier concentration N(t) (the vertical axis) and the time (the horizontal axis) in the graph of FIG. 3(a) can be approximated to the following equation:

[Equation 2]

$$N(t) = 1 + \tanh\left(\frac{t}{\Delta t}\right) \quad (2)$$

wherein $\Delta t$ is the width of the pulse light A. The Fourier transform of a time response j(t) of the detected electric current can be expressed as follows.

$$j(\omega) \propto E(\omega)N(\omega) \quad (3)$$

Therefore, in order to determine light frequencies to which the method of the present invention is responsive, it is possible to evaluate $N(\omega)$. Here, the following equations are established.

[Equation 3]

$$N(\omega) = \frac{1}{2\pi}\int_{-\infty}^{+\infty} e^{i\omega t}\left(1 + \tanh\left(\frac{t}{\Delta t}\right)\right)dt \quad (4)$$

[Equation 4]

$$E(\omega) = \frac{1}{2\pi}\int_{-\infty}^{+\infty} E(t)e^{i\omega t}dt \quad (5)$$

FIG. 3(b) illustrates the result of calculations of $N(\omega)$, wherein the pulse width $\Delta t$ of the pulse light A is used as a parameter.

The horizontal axis represents the frequency (Hz), and for example, $3 \times 10^4$ on the horizontal axis represents 300 THz, and represents the frequency of an electromagnetic wave within the 1-μm-wavelength light region. A is $N(\omega)$ when the pulse width $\Delta t$ is 15 fs, and B is $N(\omega)$ when the pulse width $\Delta t$ is 5 fs. In general, it is possible to perform the measurement until the electric current is reduced by an order of magnitude. Therefore, in the case where $\Delta t$ is 15 fs, it is possible to measure the electric field up to a frequency of 100 THz in the near-infrared region by the method according to the present invention. Further, in the case where the pulse width is 5 fs, it is possible to observe the electric field of light with a frequency of up to 250 THz near the visible radiation region.

Figure 4:
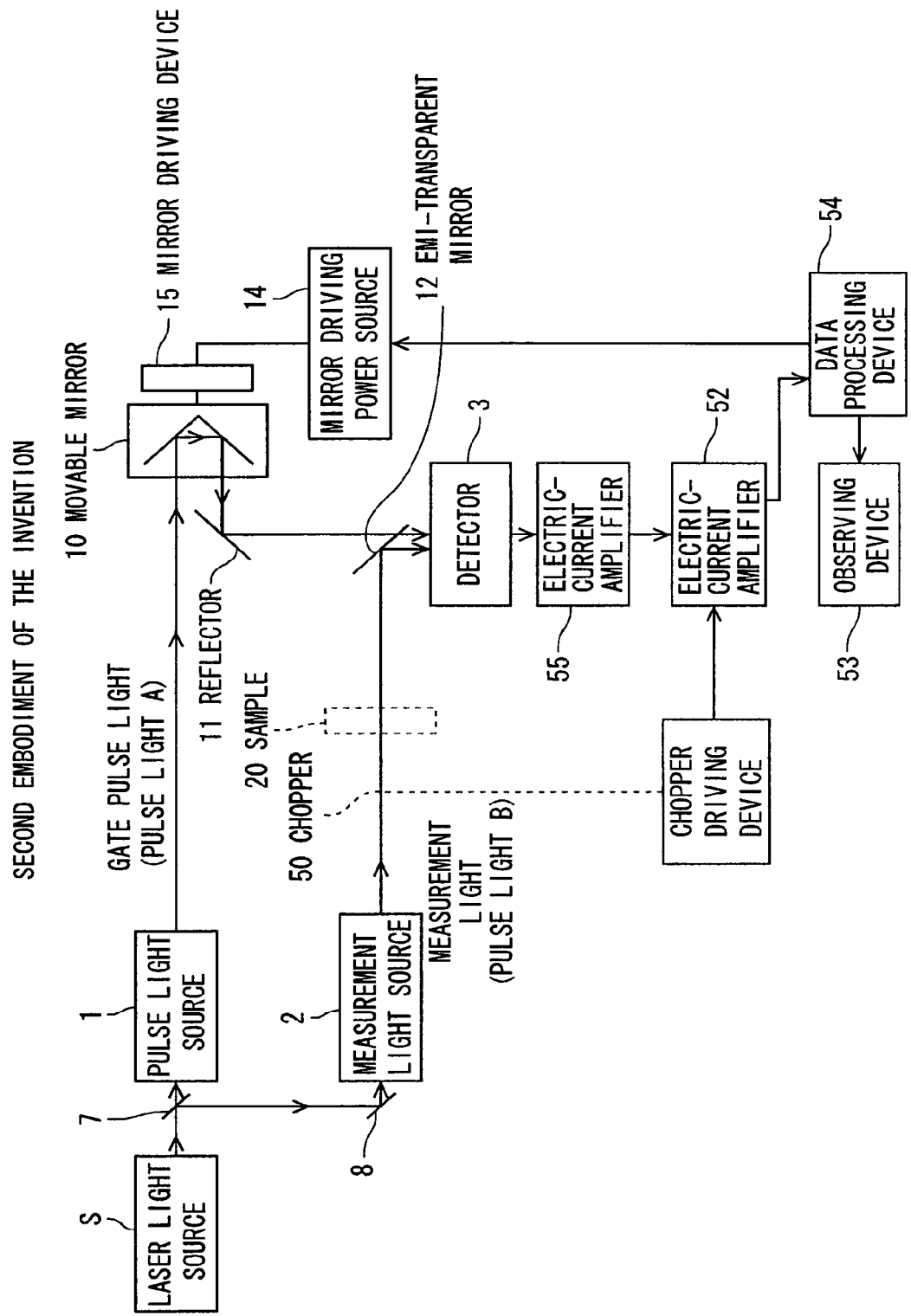
FIG. 4 is a diagram illustrating a second embodiment of the present invention.

FIG. 4 illustrates a light waveform measuring device and a complex-refractive-index measuring device according to a second embodiment of the present invention. In FIG. 4, reference symbol S is a laser light source having, for example, a wavelength of 800 nm, a pulse width of 130 fs (FWHM), a repetition frequency of 1 KHz and an output of 1 mJ. 1 is a pulse light source which generates pulse light A and is an optical parametric amplifier. For example, it is a nonlinear optical parametric amplifier which generates pulse light A having a wavelength within the range of 450 to 1600 nm and a pulse width within the range of 10 to 50 fs, on the basis of the output light from the laser light source S. 2 is a measurement-light source and is an optical parametric amplifier which generates measurement light on the basis of the output light from the laser light source S. Hereinafter, there will be described a case where the measurement light is coherent pulse light B. For example, the pulse light B is pulse light having a wavelength within the range of 1.2 to 10 μm and a pulse width of 200 fs. The pulse width of the pulse light B may be also about 1 ps for performing measurements.

3 is a detector. 7 and 12 are semi-transparent mirrors. 8 and 11 are reflectors. 10 is a movable mirror. 14 is a mirror driving power source. 15 is a mirror driving device. 20 is a sample. 52 is a high-sensitivity amplifier and is, for example, a lock-in amplifier, a boxcar integrator or the like. In the case where the gate pulse light has a high repetition frequency (for example, 100 MHz), a lock-in amplifier is effective. However, in the case where the gate pulse light has a low repetition frequency (for example, 1 MHz), a boxcar integrator can be utilized. Also, a sample-and-hold circuit and an integration circuit may be utilized to enable amplification with a high amplification factor and low noise. Hereinafter, there will be described a case of employing a lock-in amplifier. In the case of employing a boxcar integrator, there is no need for a chopper. 53 is an observing device for observing the waveform. 54 is a data processing device which performs data processing or a Fourier transform for obtaining amplitudes and phases from the measured waveform of the measurement light and obtains the complex refractive index of the sample 20. 55 is an electric-current amplifier.

The operation of the configuration of FIG. 4 will be described. The output light from the laser light source S is passed through the semi-transparent mirror 7 and is directed to the pulse light source 1. The pulse light source 1 generates pulse light A with a wavelength within the range of 450 to 1600 nm and a pulse width within the range of 10 to 50 fs, on the basis of the output light of the laser light source S. The pulse light A is reflected by the movable mirror 10, then reflected by the reflector 11, passed through the semi-transparent mirror 12, and is directed to the gap portion of the detector 3.

On the other hand, the output light from the laser light source S is reflected by the semi-transparent mirror 7 and the reflector 8 and then is directed to the measurement light source 2. The measurement light source 2 generates pulse light B with a wavelength within the range of 1.2 to 10 μm and a pulse width of 200 fs, on the basis of the output light of the laser light source S. The pulse width of the measurement light is not limited thereto and may be about 1 ps or more. The pulse light B is reflected by the semi-transparent mirror 12 and is directed to the gap portion of the detector 3.

When the detector 3 is irradiated with the pulse light A, as previously described with reference to FIG. 2, carriers are generated at the electrode gap portion of the detector 3, and an electric current depending on the electric field intensity of the pulse light B being directed thereto at this time flows between the electrodes 31 and 31'. By continuously sweeping the movable mirror 10 through the mirror driving power source 14, the optical path length between the pulse light source 1 and the detector 3 is continuously changed, thereby continuously changing the time point at which the gap portion is irradiated with the pulse light A. By continuously changing the timing of the irradiation of the pulse light A to the gap portion with respect to the pulse light B, it is possible to obtain sampling data of the electric field of the pulse light B at respective irradiation time points.

By periodically chopping the pulse light B output from the measurement light source 2 by using, for example, a chopper driving device 51, it is possible to observe the output of the detector 3 with high sensitivity and low noise, through the lock-in amplifier 52 by using the period of chopping as a reference signal. By storing the output from the lock-in amplifier 52 in the data processing device 54 and performing a process for reproducing the waveform from the stored sampling data, it is possible to display the waveform by the observation device 53.

The data processing device 54 receives observation data output from the lock-in amplifier 52. A comparison is made between waveform data of the observed waveform of the pulse light B which does not pass through the sample 20 and waveform data of the observed waveform of the pulse light B having passed through the sample 20, and then the complex refractive index p of the sample is obtained through calculations. Further, the refractive index n of the sample with respect to the measurement light can be obtained from the real part of the complex refractive index, and the absorption coefficient α of the sample can be obtained from the imaginary part (attenuation coefficient) thereof with calculations. The complex-refractive-index measuring device according to the present invention is not limited to electric-field waveforms with smaller wavelengths than wavelengths in the near-infrared region and may employ a terahertz electromagnetic wave and the like having a greater wavelength than wavelengths in the far-infrared region.

In the case of obtaining the complex refractive index using the reflection at the sample surface in the system of FIG. 4, the system is configured to define the position of the detector and the respective optical paths such that the measurement light reflected by the sample is directed to the detector. A reflector capable of substantially completely reflecting the measurement light (a high-reflectivity reflector made of silver, gold, aluminum or the like) is placed at the position at which the sample is to be placed, and a comparison is made between the waveform of the measurement light reflected by the sample and the waveform of the measurement light reflected by the reflector which have been observed in real time, similarly to the case of using transmitted light. Then, the complex refractive index is obtained.

Figure 5:
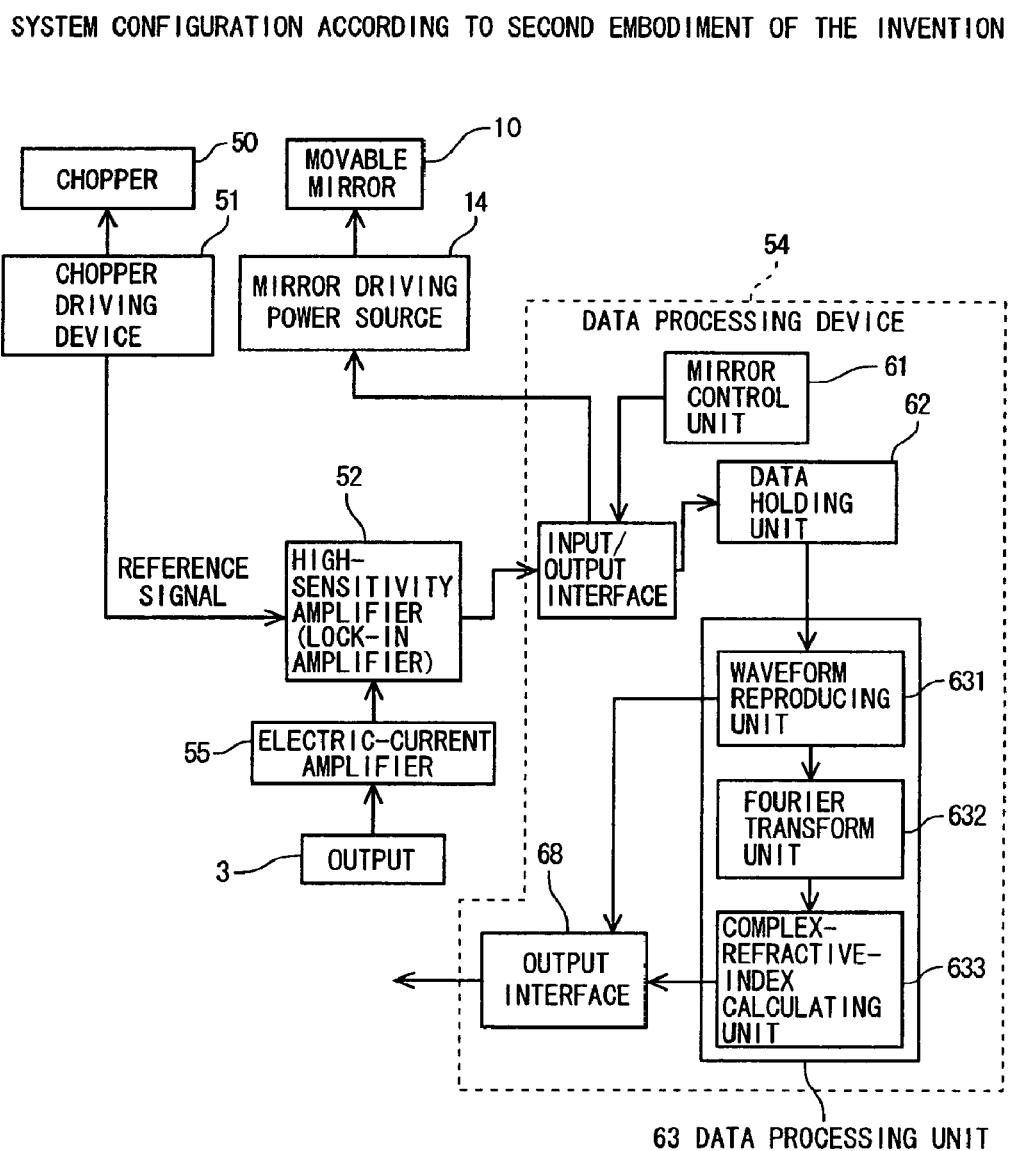
FIG. 5 is a diagram illustrating a system configuration according to the second embodiment of the present invention.

FIG. 5 is a system configuration according to the embodiment of the present invention. In FIG. 5, 3 is a detector. 10 is a movable mirror. 14 is a mirror driving power source (illustration of the mirror driving device 15 is omitted). 50 is a chopper. 51 is a chopper driving device. 52 is a high-sensitivity amplifier (lock-in amplifier). 54 is a data processing device which is a computer. 55 is an electric-current amplifier.

In the data processing device 54, 61 is a mirror control unit for controlling the movable mirror 10. 62 is a data holding unit for holding sampling data of the electric field of the measurement light. 63 is a data processing unit for processing the sampling data. 631 is a waveform reproducing unit for reproducing the waveform of the measurement light, on the basis of the sampling data. 632 is a Fourier transform unit for applying a Fourier transform to the reproduced waveform data. 633 is a complex-refractive-index calculating unit for calculating the complex refractive index of the sample, on the basis of the Fourier transforms of the waveforms of the measurement light having passed through the sample and the measurement light which did not pass therethrough. In the case of using the configuration of FIG. 5 only as a light-waveform measuring device, the complex-refractive-index calculating unit 633 can be eliminated.

In the configuration of FIG. 5, the mirror control unit 61 creates controlling signals for controlling the movement of the movable mirror 10, and transmits them to the mirror driving power source 14. The mirror driving power source 14 drives a mirror driving device (not shown) for the movable mirror to cause movement of the movable mirror 10. Along with the movement of the movable mirror 10, the observation data of the amplitude of the measurement light measured in real time by the detector 3 is input to the electric-current amplifier 55 where it is amplified. The electric current amplified by the electric-current amplifier 55 is input to the lock-in amplifier 52. On the other hand, the lock-in amplifier 52 receives reference signals from the chopper driving device 51 and amplifies, with low noise, the input from the electric-current amplifier 55 and the sampling data of the electric current value detected by the detector 3 through the reference signals. In the data processing device 54, the data holding unit 62 holds the measured sampling data. The sampling data is held at respective measurement times which depend on the optical path difference of the pulse light A. In the case of using the device of FIG. 5 as a complex-refractive-index determination device, sampling data is held at respective measurement times for different optical-path differences of the pulse light A, for the case where the measurement light passes through the sample and for the case where it does not pass therethrough. The waveform reproducing unit 631 reproduces the waveform of the measurement light, on the basis of the sampling data held in the data holding unit 62. The Fourier transform unit 632 applies a Fourier transform to the reproduced electric-field waveform to convert the measurement light into an expression of a frequency domain. Further, the complex-refractive-index calculating unit 633 obtains the complex refractive index of the sample, on the basis of the Fourier transforms of the real-time waveforms of the measurement light having passed through the sample and the measurement light which did not pass the sample. Moreover, the complex-refractive-index calculating unit 633 obtains the refractive index n and the absorption coefficient α of the sample, from the complex refractive index p. An output interface 68 outputs the waveform of the measurement light, and the complex refractive index, the refractive index and the absorption coefficient which have been obtained by calculations. The output interface 68 may output the result of application of a Fourier transform to the waveform of the measurement light, as required.

As a complex-refractive-index measuring device according to the present invention, the configuration of FIG. 5 may be entirely utilized as a complex-refractive-index measuring device. Also, only the data processing device may be utilized as a complex-refractive-index measuring device. In the latter case, data of an electric-field waveform observed by another measurement device is input to the data processing device and the data processing device of FIG. 5 is used for calculating a complex refractive index.

Figure 6:
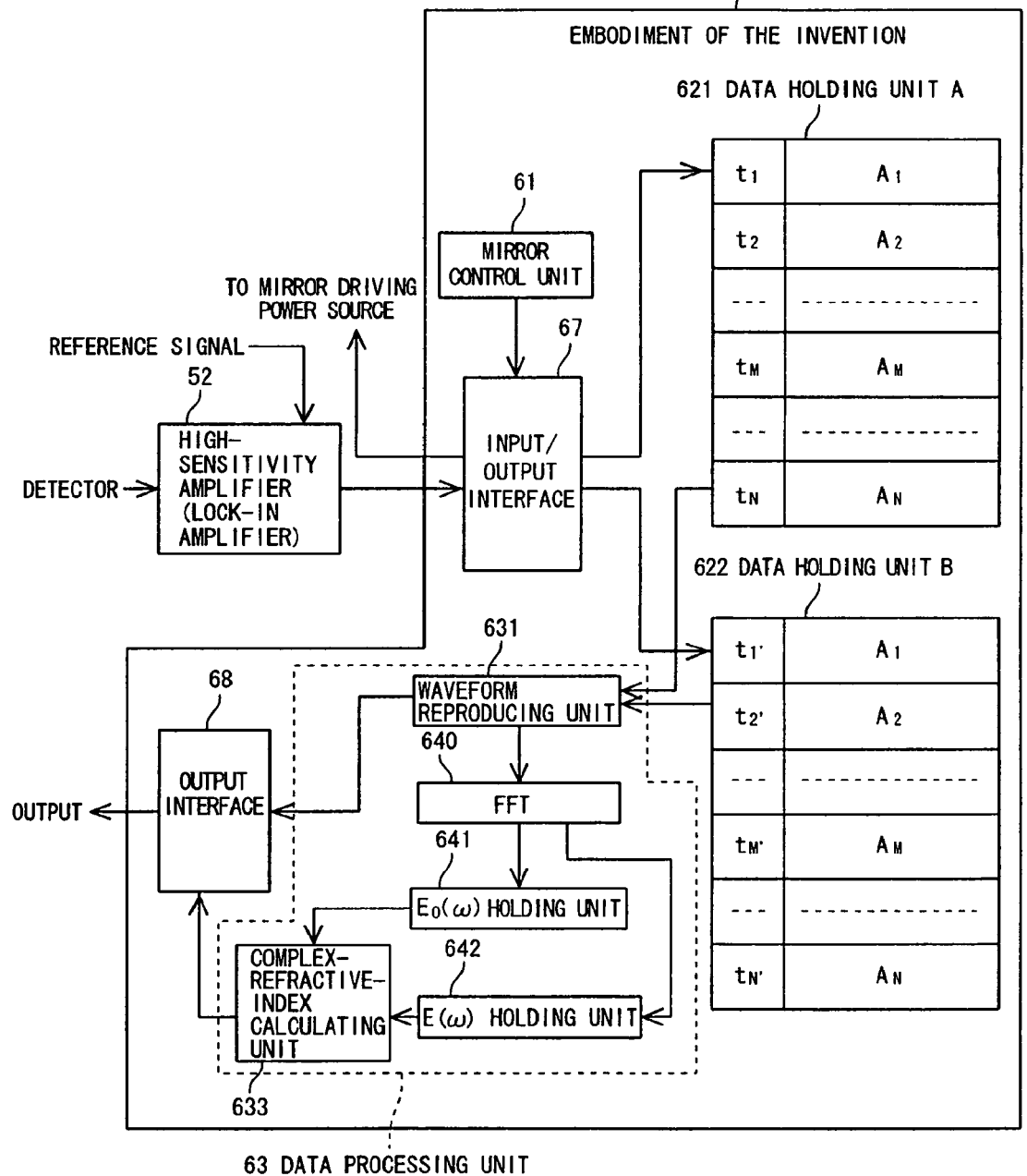
FIG. 6 is a diagram illustrating a configuration of a data processing device according to the second embodiment of the present invention.

FIG. 6 illustrates a configuration of a data processing device according to the second embodiment of the present invention. FIG. 6 illustrates the configuration relating to a data holding unit. In FIG. 6, 52 is a lock-in amplifier which receives reference signals and signals from the detector and amplifies the signals. 54 is a data processing device which is constituted by a CPU and a memory. 63 is a data processing unit. 621 is a data holding unit A which holds sampling data of the electric field of the measurement light which does not pass through the sample at respective measurement times. 622 is a data holding unit B which holds sampling data of the electric field of the measurement light having passed through the sample at respective measurement times. 67 is an input/output interface. 68 is an output interface.

631 is a waveform reproducing unit. 633 is a complex-refractive-index calculating unit. 640 is an FFT which applies a Fourier transform to the real-time waveform of the electric field (this corresponds to the Fourier transform unit 632 of FIG. 5). 641 is an $E_0(\pm)$ holding unit which holds the Fourier transform $E_0(\omega)$ of the electric-field waveform of the measurement light which does not pass through the sample. 642 is an $E(\omega)$ holding unit which holds the Fourier transform $E(\omega)$ of the electric-field waveform of the measurement light which does not pass through the sample.

There will be described an operation of the configuration of FIG. 6 for measuring the complex refractive index of the sample. The outputs of the lock-in amplifier 52 are held in the data holding unit A or the data holding unit B through the input/output interface 67. The measurement data of the measurement light which does not pass through the sample is held in the data holding unit A at respective sampling times. The measurement data of the measurement light having passed through the sample is held in the data holding unit B at respective sampling times.

In the data processing device 54, the waveform reproducing unit 631 reproduces the electric-field waveform of the measurement light having passed through the sample, on the basis of the sampling data at the respective times which is being held in the data holding unit A. Further, on the basis of the sampling data at respective times which is being held in the data holding unit B, the waveform reproducing unit 631 reproduces the electric-field waveform of the measurement light having passed through the sample. In the case of applying a Fourier transform to the electric-field waveforms, the electric-field waveforms are input to the FFT 640 to obtain a Fourier transform $E(\omega)$ of the electric-field waveform of the measurement light having passed through the sample and a Fourier transform $E_0(\omega)$ of the electric-field waveform of the measurement light which did not pass through the sample. Then, $E_0(\omega)$ and $E(\omega)$ are held in the $E_0(\omega)$ holding unit 641 and the $E(\omega)$ holding unit 642, respectively. Further, in the case of obtaining the complex refractive index and the absorption coefficient, the complex-refractive-index calculating unit 633 receives the Fourier transform $E_0(\omega)$ of the electric field of the measurement light which did not pass through the sample and the Fourier transform $E(\omega)$ of the electric field of the measurement light having passed through the sample, and obtains the complex refractive index according to the aforementioned equation (6). Further, it obtains the absorption coefficient according to the equation (8). The output interface outputs the real-time electric-field waveform, the refractive index, the attenuation coefficient and the absorption coefficient.

In the above description, the waveform of the measurement light is subjected to a Fourier transform to obtain the complex refractive index of the sample. However, it is also possible to make a comparison between the electric-field waveform of the measurement light which does not pass through the sample and the electric-field waveform of the measurement light having passed through the sample, obtain the attenuation factor from the amplitude change and obtain the refractive index from the phase change. For example, a function defining the waveform of the measurement light can be obtained by assuming a function having a parameter indicating an observed waveform, making a comparison between the function and actual observed data with a least-squares method and determining the parameter such that the difference therebetween becomes smallest. On the basis of the functions defining the waveforms of the measurement light which did not pass through the sample and the measurement light having passed through the sample, it is possible to obtain the complex refractive index, the refractive index and the absorption coefficient of the sample.

Also, in the case of observing only the waveform of the measurement light in the configuration of FIG. 6, measurement data is held in the data holding unit A (621), the waveform is reproduced by the data processing unit 63 and is output to the observing device 53. Also, the obtained waveform is subjected to a Fourier transform to output an expression of the frequency domain thereof.

Next, there will be described a method for obtaining the complex refractive index p, the refractive index n, the attenuation coefficient k and the absorption coefficient $\alpha$, on the basis of data of the real-time waveform. The electric field of the measurement light which does not pass through the sample is referred to as $E_0(t)$ and the electric field of the measurement light having passed through the sample is referred to as $E(t)$. The both electric fields are subjected to a Fourier transform which is defined by the following equation (5).

[Equation 5]

$$E(\omega) = \frac{1}{2\pi} \int_{-\infty}^{+\infty} E(t) e^{i\omega t} dt \qquad (5)$$

Assuming that the sample has a thickness of L and neglecting the influence of the end surfaces of the sample, the ratio between the Fourier transform $E(\omega)$ of the electric field of the measurement light having passed through the sample and the Fourier transform $E_0(\omega)$ of the electric field of the measurement light which did not pass through the sample is as follows. Here, $\omega$ indicates the angular frequency.

[Equation 6]

$$\frac{E(\omega)}{E_0(\omega)} = e^{-i(p(\omega)-1)L\omega/c} \qquad (6)$$

Here, $p(\omega)$ is the complex refractive index.

$$p = n + ik \qquad (7)$$

wherein n is the refractive index and k is the attenuation coefficient. There is a relationship between the absorption coefficient $\alpha$ and the attenuation coefficient k as follows, wherein c indicates the speed of light.

$$\alpha = 2k\omega/c \qquad (8)$$

As previously described, $E(\omega)$, $E_0(\omega)$ and p are complex numbers. In the aforementioned equation (6), assuming that the thickness of the sample is L, the phase difference of the measurement light which does not pass through the sample is $L\omega/c$ while the phase difference of the measurement light which has passed through the sample is $P(\omega)L\omega/c$ and the difference therebetween is indicated in the equation (6).

The aforementioned equation (6) is separated into the equations relating to the real part and the imaginary part, and therefore, it is possible to obtain the refractive index n and the attenuation coefficient k. In actual, a phase change and reflection occur at the sample surfaces. Therefore, in taking account thereof, the following equation holds, in the case where the measurement light is perpendicularly incident to the sample.

[Equation 7]

$$\frac{E(\omega)}{E_0(\omega)} = \left(\frac{2n}{n+1}\right)^2 e^{-i(p(\omega)-1)L\omega/c} \times \sum_m \left(\left(\frac{p-1}{p+1}\right) e^{-ip(\omega)L\omega/c}\right)^{2m} \quad (9)$$

In the equation (9), the following equation indicates the effect of reflection at the back surface.

[Equation 8]

$$\sum_m \left(\left(\frac{p-1}{p+1}\right) e^{-ip(\omega)L\omega/c}\right)^{2m} \quad (10)$$

The effect of reflection at the back surface is infinitely continued and the number m of reflections is cut according to the actually required accuracy. Namely, the movable mirror 10 in FIG. 5 is moved within the range which can generate an m-th reflection pulse.

While there have been described cases of utilizing a transmittance spectrum in the aforementioned description, in the case of utilizing a reflection spectrum, the following equation holds. In the case where the sample is made of a material which does not transmit light, there is a relationship between the electric field $E_0(\omega)$ of the measurement light which is not reflected and the electric field $E(\omega)$ of the reflected light, as follows.

$$E(\omega)/E_0(\omega)=(p-1)/(p+1) \quad (11)$$

$E(\omega)$, $E_0(\omega)$ and p are imaginary numbers, similarly to the aforementioned case. $E_0(\pm)$ can be obtained from measurements of a reference sample having a known p, and therefore, p of the to-be-measured sample can be obtained therefrom.

FIG. 7 is a flow chart executed by the data processing device according to the second embodiment of the present invention. FIG. 7(a) is a flow chart of the acquisition of measurement data with the data processing device 54 according to the present invention. FIG. 7(b) is a flow chart executed by the data processing unit 63 according to the present invention and is a flow chart for obtaining the complex refractive index and the absorption coefficient of the sample on the basis of measurement data.

With reference to FIG. 7, there will be described a method for acquiring measurement data with the data processing device according to the present invention (FIGS. 5 and 6 will be referred). The movable mirror 10 is controlled by the mirror control unit 61 to set the position thereof (S1). The data processing device 54 receives sampling data of the measured electric field which is output from the lock-in amplifier (S2). The sampling data of the electric field input thereto is held in a memory (data holding unit 62) (S3). It is determined whether or not a predetermined number of sampling data has been acquired (S4, 5). The processes on and after S1 are repeated until the predetermined number of sampling data is acquired. When the predetermined number of sampling data has been acquired, the real-time waveform of the electric field of the measurement light is obtained from the sampling data and is output at S6.

FIG. 7(b) illustrates a flow chart executed by a complex-refractive-index calculating unit in the data processing device according to the present invention. The Fourier transforms $E(\omega)$ and $E_0(\omega)$ of the electric fields are input thereto and held therein (S1). $E(\omega)/E_0(\omega)$ is obtained according to the equation (6) and then held therein (S2). The result of calculation of $E(\omega)/E_0(\omega)$ is divided into the real part and the imaginary part (S3). On the basis of the real part and the imaginary part of $E(\omega)/E_0(\omega)$, equations for the refractive index n and the attenuation coefficient k are created (S4). The equations are solved to obtain the refractive index n and the attenuation coefficient k (S5). On the basis of the attenuation coefficient k, the absorption coefficient α is obtained according to the equation (8) (S6). The refractive index n, the attenuation coefficient k and the absorption coefficient α are output (S7). In the case of taking account of the multiple reflections at the surface and the back surface of the sample, the equation (9) is employed at S2, instead of the equation (6) (the number m of reflections is obtained from the measurement data). Further, in the case of measuring the complex refractive index by utilizing the reflection at the sample surface, the equation (11) is employed at S2, instead of the equation (6).

Figure 8:
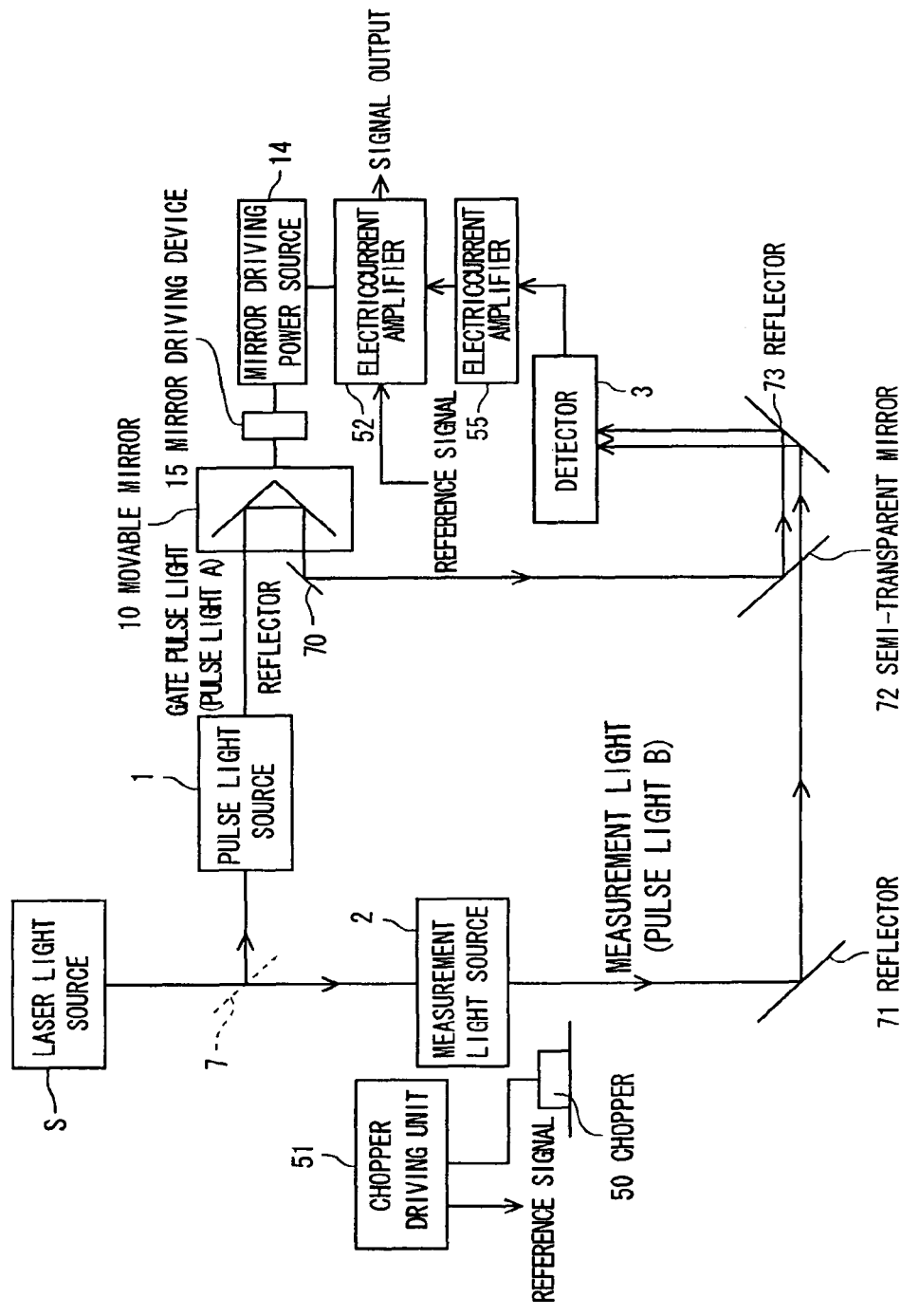
FIG. 8 is a diagram illustrating a third embodiment of the present invention.

FIG. 8 illustrates a third embodiment of the present invention. FIG. 8 illustrates a configuration for directing pulse light A and pulse light B to the same surface of the detector 3 for measuring, in real time, the amplitude of the measurement light (the pulse light B). In FIG. 8, the same reference numerals as those in FIG. 4 designate the same configurations.

In FIG. 8, a part of pulse light generated from a laser light source S is reflected by a semi-transparent mirror 7 and then is directed to a pulse light source 1. The pulse light source 1 generates pulse light A from the laser light generated from the laser light source S. The pulse light A is reflected by a movable mirror 10, then is repeatedly reflected by a reflector 70, a semi-transparent mirror 72 and a reflector 73 and is directed to a detector 3. Also, a part of the pulse light generated from the laser light source S is transmitted through the semi-transparent mirror 7 and then is directed to a measurement light source 2. The measurement light source 2 generates pulse light B as measurement light, on the basis of the laser light generated from the laser light source S. The pulse light B is chopped by a chopper 50, then is reflected by a reflector 71, is transmitted through the semi-transparent mirror 72, then is reflected by the reflector 73 and then is directed to the detector 3.

The carriers generated in the detector 3 by the gate light pulse A and the electric field of the pulse light B generate an electric current, and the electric current is amplified by an electric-current amplifier 55, and then is input to a lock-in amplifier 52. The lock-in amplifier 52 measures the electric current generated in the detector 3 by using signals from the chopper driving device 51 as reference signals, wherein the signals have a period corresponding to that of chopping of the pulse light B. By moving the movable mirror 10, an optical-path length of the pulse light A is changed to change the timing of sampling. The lock-in amplifier detects sampling data at respective times with low noise, and transfers the measurement data to an observing device 53 and a data processing device 54. The operation of the data processing device 54 is the same as that of FIG. 4, and therefore, description thereof is omitted herein.

In the configuration of FIG. 8, it is possible to employ a boxcar integrator instead of the lock-in amplifier 52, in the case where the gate pulse light has a low repetition frequency. In this case, it is possible to perform the measurement without using the chopper. Also, it is possible to employ a sampleand-hold circuit and an integrating circuit to enable amplification with a high amplification factor and low noise.

FIGS. 9(a) and 9(b) illustrate a fourth embodiment of the present invention. FIGS. 9(a) and 9(b) illustrate a configuration for acquiring sampling data with plural optical-path differences and with a single irradiation of the gate pulse light for measuring the electric field of the measurement light at different times. FIGS. 9(a) and 9(b) illustrate, as an example, a case of using four reflectors for generating four optical-path differences with a single irradiation of the gate pulse light (a first method for acquiring sampling data with plural optical-path differences and a single irradiation of the gate pulse light).

In FIG. 9(a), 3 is the detector. 10 is the movable mirror. 11 is a reflector. 81, 82 and 83 are semi-transparent mirrors. 14 is a mirror driving power source. 15 is a mirror driving device. 84 is a reflector. A distance between the semi-transparent mirrors 81 and 82 is $d_1$, a distance between the semi-transparent mirrors 82 and 83 is $d_2$, and a distance between the semi-transparent mirrors 83 and 84 is $d_3$. The distances $d_1$, $d_2$ and $d_3$ are defined such that the optical-path length of the gate light is stepwise changed. The measurement light is beam light so that the respective gates of the detector 3 are concurrently irradiated therewith. 91 is an amplifier 1, 92 is an amplifier 2, 93 is an amplifier 3, and 94 is an amplifier 4. The amplifier 1, the amplifier 2, the amplifier 3 and the amplifier 4 amplify electric currents output from respective electrodes. Each of the amplifiers (91, 92, 93 and 94) is constituted by an electric-current amplifier and a lock-in amplifier, and receives and amplifies signals from the respective electrodes of the detector 3 with a high amplification factor and low noise, by using driving signals from a chopper driving device (not shown) as reference signals. The outputs from the respective amplifiers are transferred to the observing device 53 and the data processing device 54. A sequence for acquiring sampling data of the electric field of the measurement lights at different times with a single irradiation of gate pulse light can be realized by performing measurements in plural measurement sequences employing different optical-path lengths of the gate pulse light and processing the observation data, which enables efficient, high-speed measurement of the waveform of the electric field of the measurement light. As will be described later, it is possible to acquire sampling data for reproducing a real-time waveform of the electric field in a single measurement sequence. In the case where the gate pulse light has a low repetition frequency, it is possible to employ a boxcar integrator, in the amplifiers, instead of the lock-in amplifier. In this case, it is possible to perform measurements without using the chopper for the measurement light. Also, it is possible to employ a sample-and-hold circuit and an integrating circuit to enable amplification with a high amplification factor and low noise.

FIG. 9(b) is a plan view of the detector 3. 101 and 101' are electrodes, wherein gap portions between the respective opposing electrodes are irradiated with the light pulse of the gate light. Similarly, 102 and 102', 103 and 103' and 104 and 104' are electrodes.

In the configuration illustrated in FIGS. 9(a) and 9(b), the measurement light beam is directed to the respective gaps between the electrodes. The length from the gap between the uppermost electrodes to the gap between the lowermost electrodes may be set to 50 μm or less in the case of four electrodes, and therefore, the diameter of the measurement light beam may be set to around the value. Even in the case of eight electrodes, the length may be set to 100 μm or less and this length may be made equal to or less than the diameter of the measurement light beam.

The operation of the configuration of FIG. 9 will be described. Pulse light A as the gate pulse light is reflected by the movable mirror 10 and then reflected by the reflector 11, and a part thereof is reflected by the semi-transparent mirror 81 while the remaining part is transmitted therethrough. The pulse light A transmitted through the semi-transparent mirror 81 is directed to the gap between the electrodes 101 and 101' of the detector 3. Further, the pulse light A transmitted through the semi-transparent mirror 81 is partially reflected by the semi-transparent mirror 82 while the remaining part is transmitted therethrough. The pulse light A reflected by the semi-transparent mirror 82 is directed to the gap between the electrodes 102 and 102'. Further, the pulse light A transmitted through the semi-transparent mirror 82 is partially reflected by the semi-transparent mirror 83 while the remaining part is transmitted therethrough. The pulse light A reflected by the semi-transparent mirror 83 is directed to the gap between the electrodes 103 and 103'. The pulse light A transmitted through the semi-transparent mirror 83 is reflected by the reflector 84 and then is directed to the gap between the electrodes 104 and 104'.

On the other hand, the respective gaps between the electrodes are concurrently irradiated with the measurement light which is a single light beam (the gate pulse light incident to the semi-transparent mirrors 81, 82 and 83 and the reflector 84 is a collimate light). The times at which the respective electrodes are irradiated are delayed from one another by the amounts corresponding to the distances $d_1$, $d_2$ and $d_3$ between the respective semi-transparent mirrors and the reflector. Accordingly, the to-be-sampled electric currents output from the respective electrodes have amplitudes corresponding to the electric fields of the pulse light B at the times at which the respective gaps are irradiated with the pulse light A. As described above, it is possible to measure the electric fields of the measurement light at different phases through a single irradiation of the gate pulse light. By moving the movable mirror for changing the optical-path length and by repeating the aforementioned measurement, it is possible to efficiently measure the electric fields of the measurement light at many different phases.

Figure 10:
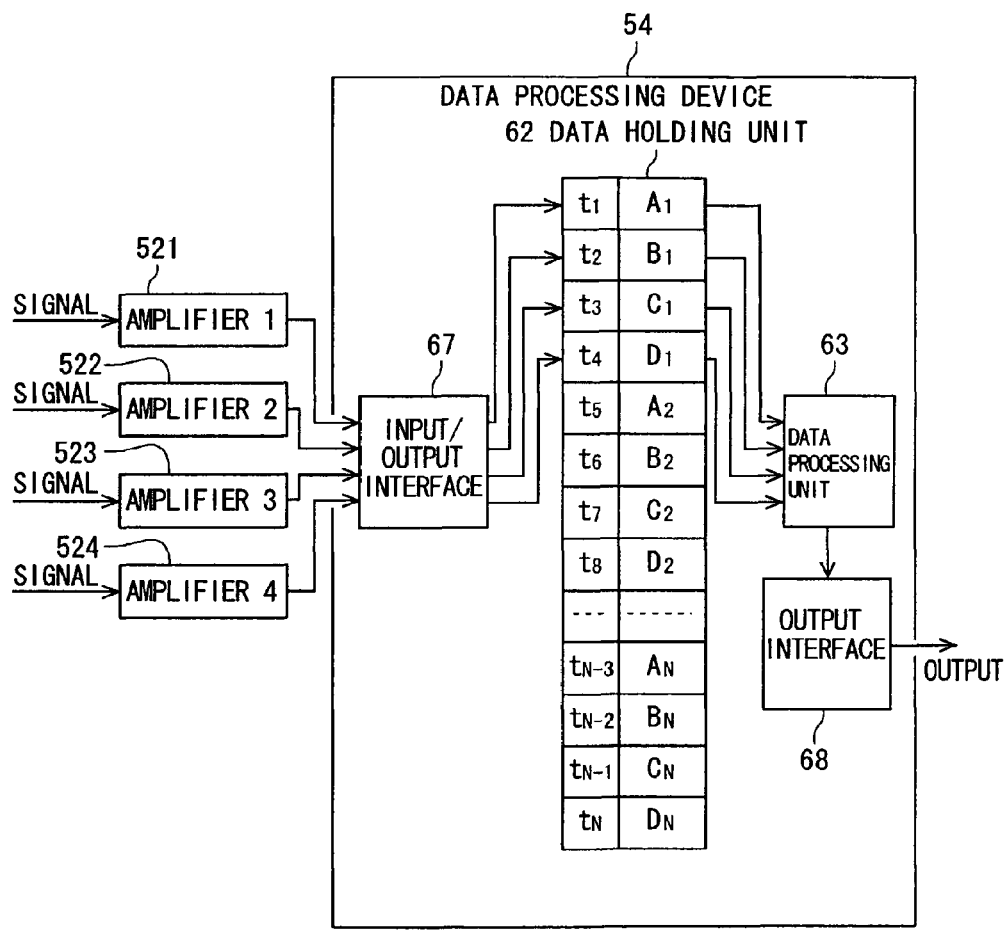
FIG. 10 is a diagram illustrating a configuration of a data processing device according to the fourth embodiment of the present invention.

FIG. 10 is a configuration of a data processing device according to the fourth embodiment of the present invention. FIG. 10 illustrates the configuration relating to the data holding unit, and the data processing unit 63 is the same as that of FIG. 5. In FIG. 10, signals from the respective pairs of electrodes of the detector (signals 1 (signals extracted from the electrodes 101 and 101'), signals 2 (signals extracted from the electrodes 102 and 102'), signals 3 (signals extracted from the electrodes 103 and 103') and signals 4 (signals extracted from the electrodes 104 and 104')) are input to the amplifier 1, the amplifier 2, the amplifier 3 and the amplifier 4, respectively. The signals amplified by the amplifier 1, the amplifier 2, the amplifier 3 and the amplifier 4 are input to the data processing device 54. The respective signals ($A_1$, $B_1$, $C_1$ and $D_1$) are held in the data holding unit 62 in association with information indicating the times ($t_1$, $t_2$, $t_3$ and $t_4$) at which the detector 3 is irradiated with the respective measurement lights.

Then, the movable mirror is moved, and thereafter, signals ($A_2$, $B_2$, $C_2$ and $D_2$) obtained at times ($t_5$, $t_6$, $t_7$ and $t_8$) are held in the data holding unit 62. Similarly, the movable mirror 10 is moved, and thereafter, sampling data of the amplitudes of the measurement light obtained from the respective pairs of electrodes at respective measurement times is obtained and is held in the data holding unit 62.

On the basis of the sampling data of the amplitudes of the measurement light at respective times, the data processing unit 63 obtains the waveform of the electric field of the measurement light. In the case of outputting only the waveform of the measurement light, the data processing unit 63 displays the waveform on the observing device. Also, the waveform may be subjected to a Fourier transform and the measurement light may be displayed in an expression of the frequency domain. In the case of measuring the complex refractive index of the sample, the electric fields of the measurement light having passed through the sample and the measurement light which does not pass through the sample are obtained, the waveforms of the respective electric fields are obtained and then the respective waveforms are subjected to a Fourier transform similarly to the aforementioned method, and the complex refractive index, the refractive index and the absorption coefficient are obtained and output according to the aforementioned method.

FIGS. 11(a) and 11(b) illustrate a method for generating optical-path differences among the respective gaps with the gate pulse light directed to the respective gaps between the electrodes on the detector 3 without using the semi-transparent mirrors 81, 82 and 83 and a reflector corresponding to the reflector 84 or with only a single reflector (a second method for acquiring sampling data with plural optical-path differences and a single irradiation of the gate pulse light), according to the forth embodiment (see FIG. 9) of the present invention.

In FIGS. 11(a) and 11(b), 41 is gate pulse light (the pulse light A) having a beam diameter D. In the present embodiment, the gate pulse light is directed to the detector 3 at an angle θ with respect to a normal line of the surface of the detector 3. At this time, there is generated a optical-path difference D tan θ between a point A and a point B on the detector 3. Accordingly, by placing the electrodes such that the respective gaps between the electrodes of the detector 3 are formed between the point A and the point B, it is possible to acquire sampling data of the electric field at four points, at the same time.

FIG. 11(b) illustrates an enlarged view of the relationship between the gate pulse light 41 and the electrode gaps on the detector 3, exemplifying a case where the detector 3 has four electrode gaps thereon. In FIG. 11(b), 101, 102, 103 and 104 are electrodes on the detector 3. As the gate pulse light 41, reflected light from the movable mirror 10 illustrated in FIG. 9 may be directly diagonally directed to the detector 3. Also, the reflected light from the movable mirror 10 may be reflected by a single reflector and then diagonally directed to the detector 3. FIGS. 9 and 11 illustrate, as an example, a method for measuring four optical-path differences with a single irradiation of the gate pulse light. However, even in the case where the number of samplings of the electric field is eight or more, it is also possible to measure the optical-path differences thereamong with a single irradiation of the gate pulse, as will be described later. This enables acquisition of sampling data for reproducing the electric-field waveform through a single measurement, without using the movable mirror 10.

More specifically, plural optical-path differences obtained with a single irradiation of the gate pulse light as in FIGS. 11(a) and 11(b) are as follows. Assuming that the beam diameter of the gate pulse light 41 is 1 cm and the incidence angle θ is 45 degrees, there is generated a optical path difference of 1 cm between the points A and B on the detector 3. This optical path difference corresponds to a time of 33 ps. The required optical path difference is varied depending on the measurement light. A far infrared radiation with a wavelength of 300 μm has a period of 1 ps, and in this case, an optical path difference of a few picoseconds is sufficient for acquiring data for obtaining the electric-field waveform. In the case where the measurement light has a smaller wavelength and a smaller period, a smaller optical-path difference can be sufficient. However, in order to reproduce the waveform, it is necessary that the time interval measured between adjacent electrodes (for example, the interval between the electrodes 101 and 102 in FIG. 9, and hereinafter, it will be referred to as a vertically-adjacent electrode interval) is made smaller. By setting the vertically-adjacent electrode interval to a small interval depending on the frequency of the measurement light and also by providing many electrodes adjacent to one another in the vertical direction between the points A and B on the detector 3, it is possible to acquire sampling data enough for reproducing the electric-field waveform with a single sampling.

Even when the vertically-adjacent electrode interval can not be made small, it is possible to reduce the optical-path difference between the points A and B on the detector 3 by reducing θ. As described above, the present invention enables acquiring sampling data of the electric field, with plural optical-path differences, without moving the movable mirror 10.

The aforementioned method for acquiring plural sampling data for the electric-field waveform with a single irradiation of the gate pulse light is not limited to electromagnetic waves in the near infrared range and may be applied to methods for measuring in real time the electric-field waveforms of terahertz electromagnetic waves, visible light and the like.

Figure 12:
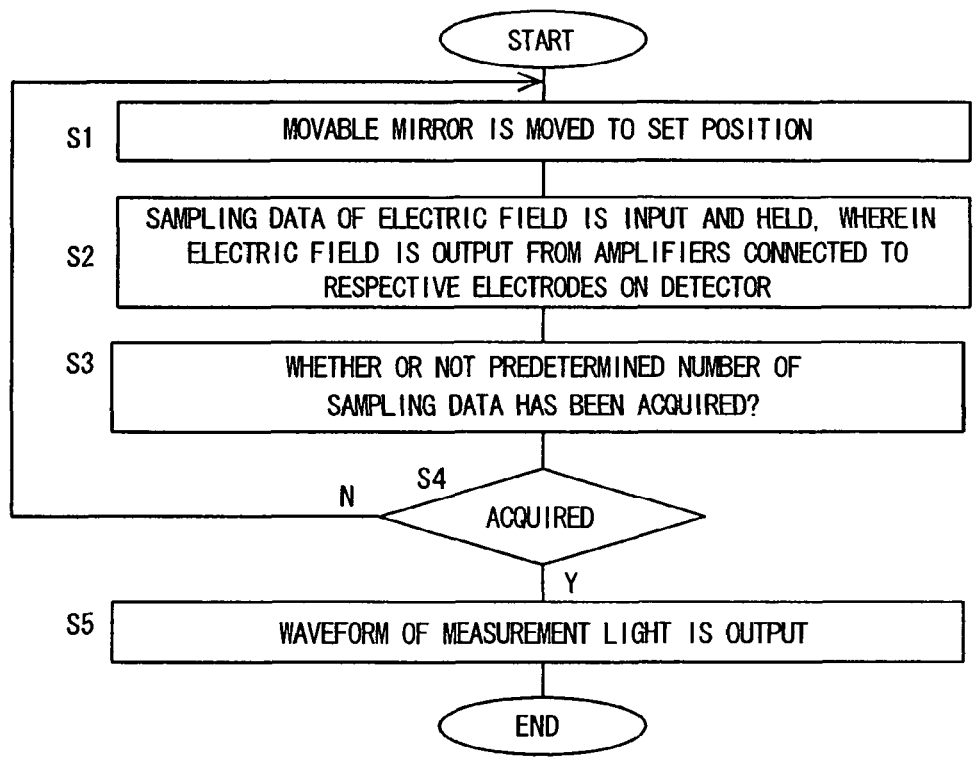
FIG. 12 is a flow chart executed in a data processing device according to the fourth embodiment of the present invention.

FIG. 12 is a flow chart executed in the data processing device according to the fourth embodiment of the present invention. With reference to FIG. 12, the operation of the data processing device according to the fourth embodiment of the present invention will be described (FIGS. 9 and 10 will be referred). The movable mirror 10 is moved by the mirror control unit 61 to set the position thereof (the control of the movable mirror 10 is the same as that performed by the mirror control unit 61 in FIG. 5) (S1). Sampling data of the electric field of the measurement light is input and held therein (S2), wherein the electric field of the measurement light has been measured by the respective electrodes on the detector 3 (the respective pairs of electrodes such as the electrodes 101 and 101') and then amplified by the amplifiers (the amplifier 1, the amplifier 2, the amplifier 3 and the amplifier 4) corresponding to the respective electrodes. It is determined whether or not a predetermined number of sampling data of observation data has been acquired (S3, S4). When it has not be acquired, the processes on and after S1 are repeated. When the predetermined number of sampling data has been acquired, the held sampling data is subjected to data processing to obtain and output the waveform (S5). A Fourier transform may be applied to the obtained waveform to determine and output an expression of the measurement light in the frequency domain, at S5.

Further, in the case of obtaining the refractive index and the absorption coefficient of the sample on the basis of the real-time observation data, the refractive index and the absorption coefficient of the sample can be calculated according to the aforementioned flow chart of FIG. 7(b). Namely, as previously described, on the basis of Fourier transforms of the amplitude data of the measurement light which does not pass through the sample and the measurement light having passed through the sample, the complex refractive index is obtained, and then, the refractive index and the absorption coefficient are obtained.

Figure 13:
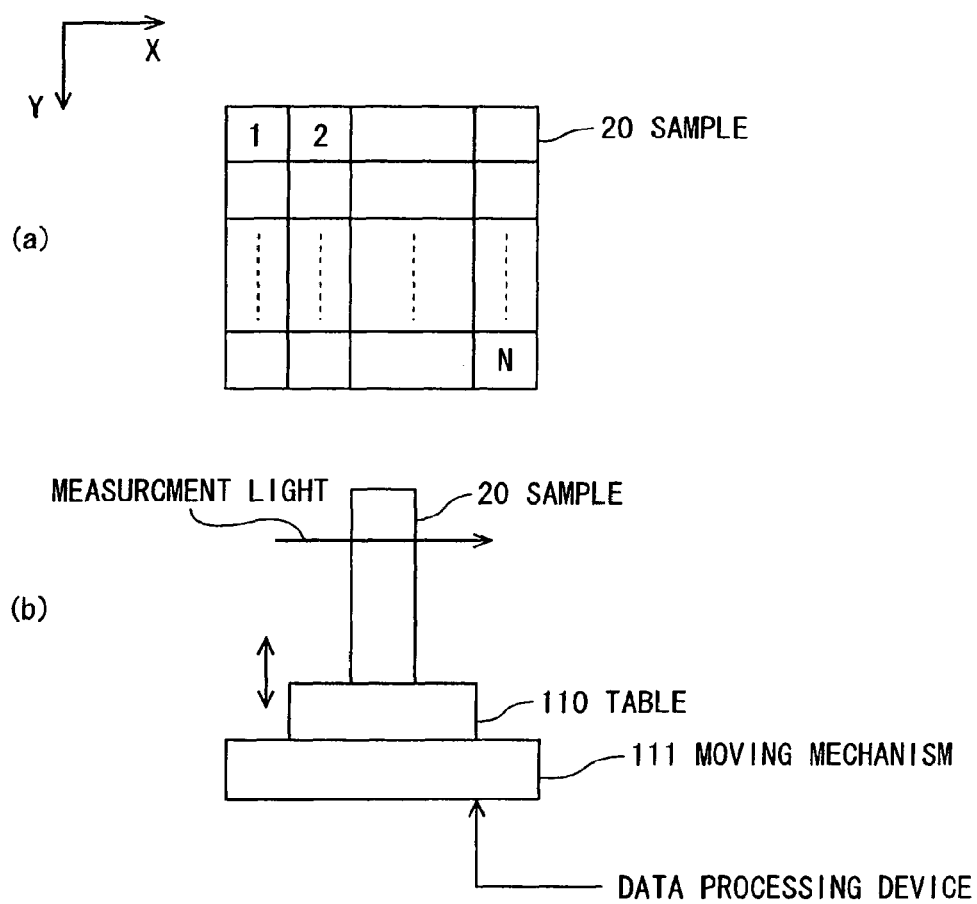
FIG. 13 is a diagram illustrating a fifth embodiment of the present invention.

FIGS. 13(a) and 13(b) illustrates a fifth embodiment of the present invention, wherein there is illustrated a case of measuring the complex refractive index of the sample at plural points on a two-dimensional surface of the sample. In this case, the sample to be measured is placed on a table capable of moving in the horizontal and vertical directions, and the electric field of the measurement light is measured at respective points on a two-dimensional surface of the sample in such a manner that observation data is acquired at an arbitrary point on the plain of the sample, and thereafter, the sample is moved and observation data is acquired at a next point thereon. By examining the complex refractive indexes at the respective points, it is possible to determine the uniformity of the sample over the plain.

In the case of measuring the complex refractive index with measurement light which does not transmit through the sample, the waveform of the measurement light reflected at the sample surface is measured. In this case, a reflector (a high-reflectivity reflector made of silver, gold, aluminum or the like) is placed instead of the sample of FIG. 13 and the waveform of the measurement light is observed in real time, by the detector 3. Further, on the basis of the waveforms obtained from the observation data of the amplitude of the measurement light reflected by the sample and the amplitude of the measurement light reflected by the reflector, the respective waveforms are subjected to a Fourier transform and a comparison is made therebetween to obtain the complex refractive index. In this case, the reflectivity of the reflector must be taken into account.

In FIGS. 13(a) and 13(b), 20 is a sample. 110 is a table which is placed on a moving mechanism 111 and is movable in the vertical direction and in the direction perpendicular to the paper. 111 is the moving mechanism for moving the table 110. The movement of the moving mechanism 111 is controlled by the data processing device. By continuously moving the table 110 in the vertical direction and in the direction perpendicular to the paper, the electric field of the measurement light is measured at respective points of the sample (points 1, 2, . . . , N illustrated in FIG. 13(a)).

Figure 14:
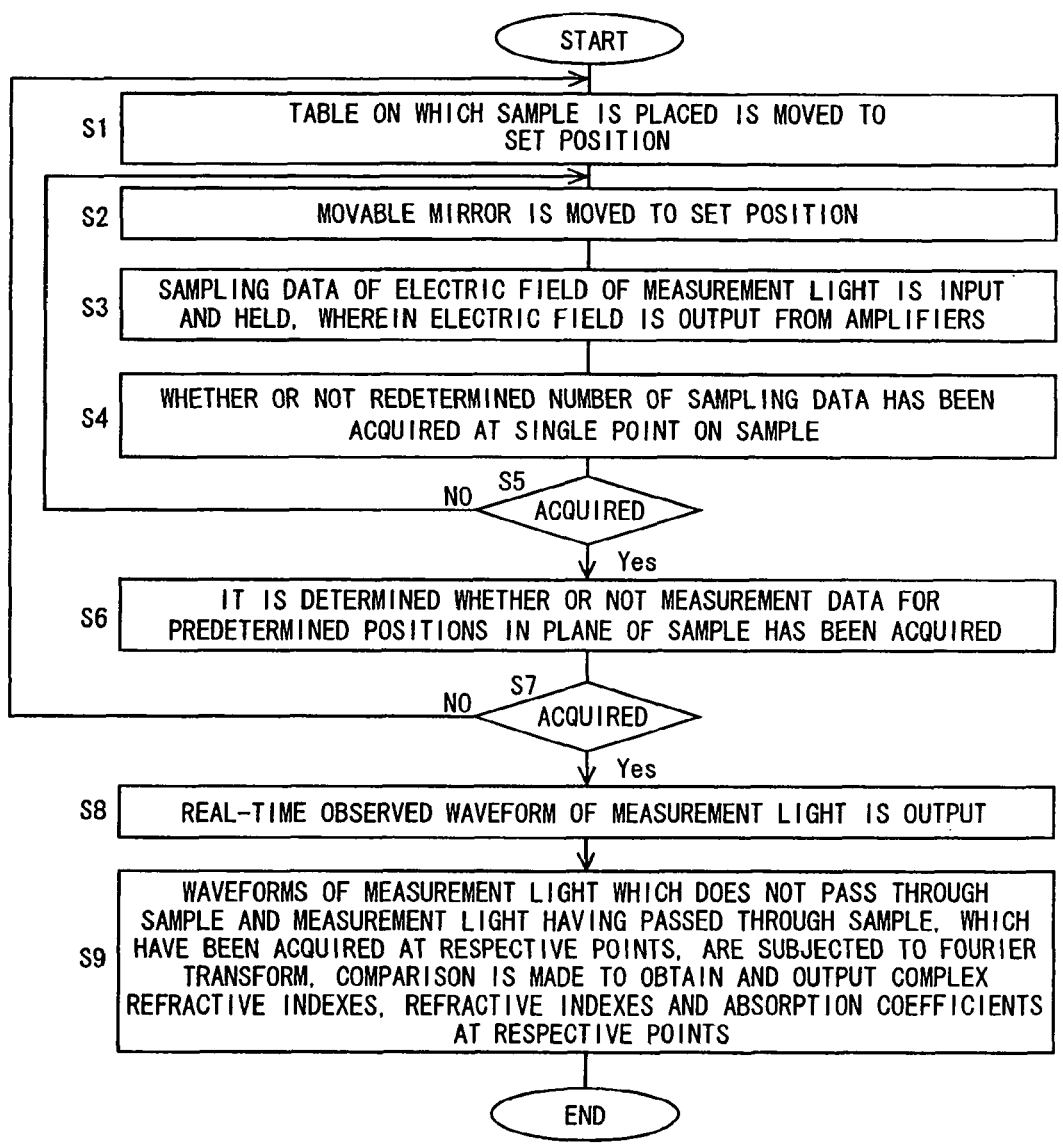
FIG. 14 is a flow chart executed in a data processing device according to the fifth embodiment of the present invention.

FIG. 14 is a flow chart according to the fifth embodiment of the present invention. The sample table on which the sample is placed is moved to set the position thereof (S1). The movable mirror is moved to set the position thereof (S2). Sampling data of the real-time waveform of the measurement light output from the lock-in amplifier is input and held (S3). It is determined whether or not a predetermined number of sampling data has been acquired at a single point on a plain of the sample (S4 and S5). When the predetermined number of sampling data has not been acquired, the processes on and after S2 are repeated. When the predetermined number of sampling data has been acquired, it is determined whether or not a predetermined number of measurement data has been acquired within the plain of the sample at S6 (S5 and S6). When measurement data has not been acquired at predetermined positions within the plain, the processes on and after S1 are repeated. When measurement data has been all acquired at the predetermined positions within the plain, the waveform of the measurement light is obtained and output at S8. Further, in the case of using the device as a complex-refractive-index measuring device, the waveforms of the measurement light which does not pass through the sample and the measurement light having passed through the sample, which have been obtained for the respective points, are subjected to a Fourier transform, and a comparison is made therebetween to obtain and output the complex refractive index, the refractive index and the absorption coefficient at the respective points (S9).

While, in the above description, the refractive index and the absorption coefficient are obtained on the basis of the Fourier transforms of the observation data of the measurement light which did not pass through the sample and the measurement light having passed through the sample, it is also possible to define a function indicating the measurement light on the basis of the waveform of the measurement light as previously described, make a comparison between the functions of the measurement light which has passed through the sample and the measurement light which did not pass through the sample to obtain the refractive index and the absorption coefficient. By configuring the detector and the irradiation of the gate pulse light to the detector as in FIG. 9, it is possible to acquire plural sampling data of the electric-field waveform of the measurement light with different optical-path differences and with a single irradiation of the gate pulse light.

The configurations according to the present invention have been described in the first to fifth embodiments. Hereinafter, there will be described the result of demonstrations of the detection performance of the detector (3) which has been described in the aforementioned embodiments.

Figure 15:
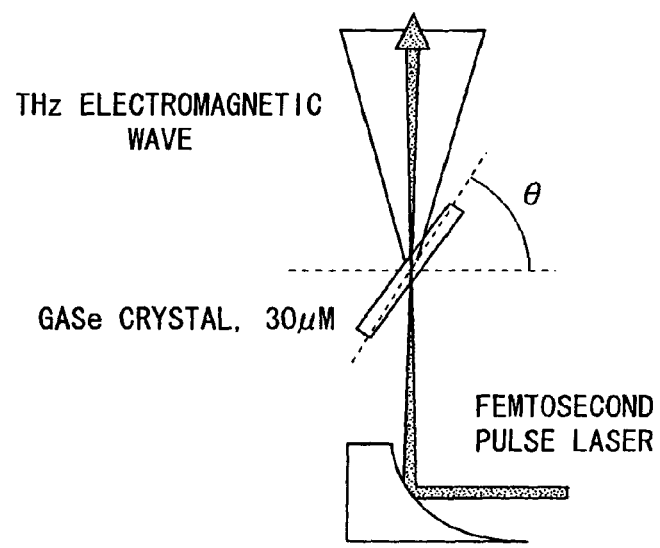
FIG. 15 is a view illustrating a lasing mechanism for a terahertz electromagnetic wave according to the present invention.

FIG. 15 is a view illustrating, in detail, the measurement-light source (2) in FIGS. 1, 4 and 8, wherein there is illustrated a mechanism for lasing a terahertz electromagnetic wave as the measurement light. In this mechanism, laser light is directed to a semiconductor crystal to generate a terahertz electromagnetic wave through the non-linear optical effects of the semiconductor. Such a mechanism is disclosed in, for example, Patent Document 1 and Patent Document 2. However, in the present tests, electromagnetic waves with higher frequencies than those of terahertz electromagnetic waves disclosed therein were generated.

Patent Document 1: U.S. Pat. No. 5,952,828

Patent Document 2: U.S. Pat. No. 6,111,416

Patent Documents 1 and 2 relate to inspection devices and methods using electromagnetic waves in an opened space and disclose terahertz generating mechanisms and receiving mechanisms for sensing using terahertz electromagnetic waves. Patent Document 2 discloses a configuration which employs GaAs as an emitter and also employs a crystal of ZnTe, GaAs, CdTe, CdZnTe, or an organic DAST as the crystal of the detector. Further, it employs a laser having a pulse width greater than 100 fs.

Patent Document 1 defines 10 GHz and 5 THz as detectable frequency regions, while Patent Document 2 defines 37 THz as a detectable frequency region.

Figure 16:
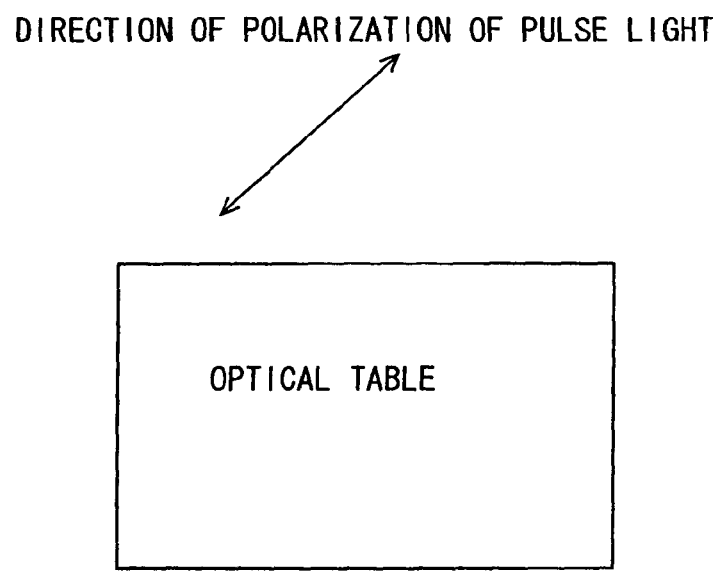
FIG. 16 is a view illustrating a polarization angle of a laser directed to a semiconductor crystal according to the present invention.

On the other hand, with the lasing mechanism used in the present tests, terahertz electromagnetic waves with frequencies of up to 67 THz could be generated by directing a femtosecond pulse laser to a crystal. In this case, a GaSe crystal with a crystal plane (001) and a thickness of 30 μm was employed as the crystal and this crystal was inclined at an angle of 70 degrees as illustrated in FIG. 15. FIG. 15 is a plan view from above the optical table. FIG. 16 illustrates the direction of polarization of the pulse light when viewed from the rear side in the direction of irradiation of the pulse laser. As illustrated in the figures, the pulse light is polarized by 45 degrees during irradiation thereof.

When θ was 20 degrees, a peak occurred at about 9 THz, and the peak tended to shift to the higher-frequency side as the angle was gradually increased. When θ was 70 degrees, a peak occurred at 35 THz. At this time, generation of electromagnetic waves having frequencies of up to 67 Hz was detected by a conventional detector.

The conventional detector included a spectroscope (with 6-μm blazes) and a Mercury Cadmium Telluride (MCT) and has proven to have a detection sensitivity of up to 90 THz.

Figure 17:
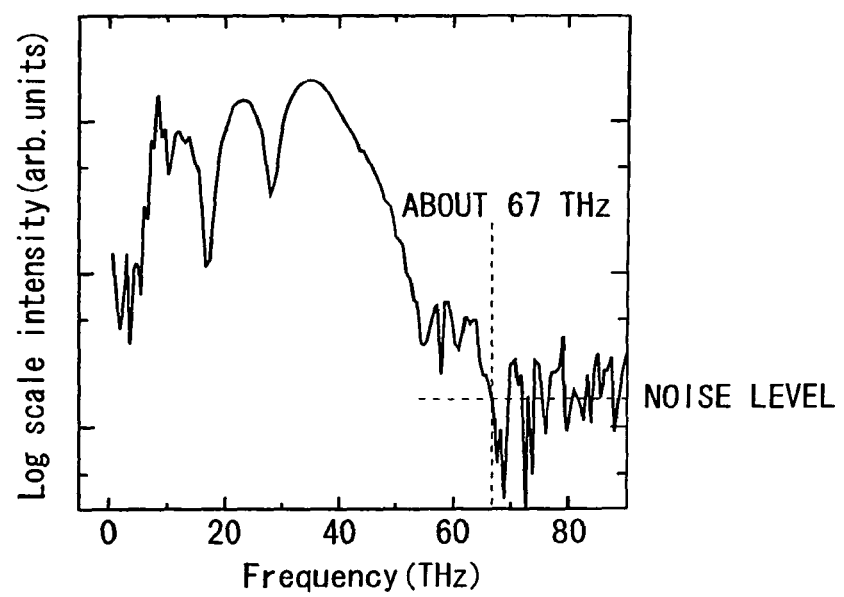
FIG. 17 is a view illustrating the result of detection with a detector according to the present invention.
Figure 18:
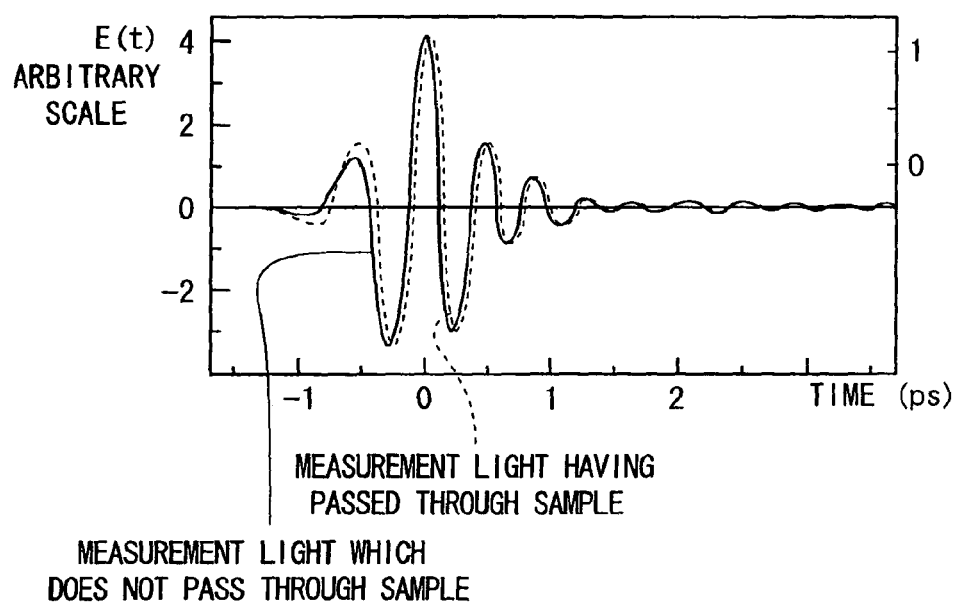
FIG. 18 is an explanation view of means for solving problems.

FIG. 17 is a semi-log graph illustrating the result of detection with the detector (3) according to the present invention, wherein the horizontal axis represents the frequency and the vertical axis represents the electric field intensity. As illustrated in the figure, it is proven that normal reception was performed from a low frequency near 0 THz to 67 Hz reaching a noise level.

As previously described, sampling data of the electric field can be continuously acquired through the movement of the movable mirror (10), and the lower limit of the detectable frequency is 10 GHz or more, and more particularly, is 0.1 THz or more.

Further, in order to perform detection of higher frequencies, it is possible to employ a laser with a smaller pulse width. However, there have been developed lasers with pulse widths of 5 fs or less, and therefore, provision of stable attosecond pulse lasers with pulse widths of 1 fs or less can be conceived. By the use of them, the present invention enables detection of high frequencies of 100 THz or more. For example, in the case where the pulse width is 1 fs or less, detection of up to 1000 THz can be realized in theory.

In the present embodiment, a pulse laser with a pulse width of 100 fs or less and of about 10 fs is employed.

The invention claimed is:

1. A light-waveform measuring device comprising: gate-pulse-light generating means; measurement-light generating means; and light-detecting means for detecting measurement light,
wherein both of gate pulse light and measurement light are coherent lights, the measurement light is coherent light having a wavelength longer than that of 100 THz, the gate pulse light has a pulse width smaller than a period of the measurement light, the gate pulse light is directed to the light-detecting means to generate carriers therein, a physical quantity based on the carriers is measured, and an electric field of the measurement light is measured on the basis of the physical quantity.

2. The light-waveform measuring device according to claim 1, wherein the gate pulse light has a pulse width of 10 fs or less.

3. The light-waveform measuring device according to claim 2, wherein the detector is constituted by a pair of electrodes which are placed on a substrate with a small gap provided therebetween, the substrate generates electrical charge when irradiated with light and the physical quantity is an electric current.

4. The light-waveform measuring device according to claim 1, wherein the detector is constituted by a pair of electrodes which are placed on a substrate with a small gap provided therebetween, the substrate generates electrical charge when irradiated with light and the physical quantity is an electric current.

5. The light-waveform measuring device according to claim 1, wherein the measurement light is light with a frequency of 0.1 THz to 67 THz.

6. The light-waveform measuring device according to claim 1, wherein the measurement light is light with a frequency of 0.1 THz to 67 THz.

7. A light-waveform measuring device comprising: gate-pulse-light generating means; measurement-light generating means; and light-detecting means for detecting measurement light,
both of gate pulse light and measurement light being coherent lights, the measurement light being a coherent electromagnetic wave or coherent visible light having a wavelength smaller than those of terahertz electromagnetic waves, the gate pulse light having a pulse width smaller than a period of the measurement light, the gate pulse light being directed to the light-detecting means to generate carriers therein, a physical quantity based on the carriers being measured, and an electric field of the measurement light being measured on the basis of the physical quantity, wherein
plural pairs of electrodes are provided, there are provided different optical-path differences for the gate pulse light directed to the gaps between the respective pairs of electrodes, and the physical quantities generated in the respective gaps between the electrodes are acquired as sampling data, with the plural optical-path differences and with a single irradiation of the gate pulse light to measure the electric field of the measurement light.

8. The light-waveform measuring device according to claim 7, wherein the gate pulse light is directed to the plural pairs of electrodes diagonally with respect to the surfaces of detection electrodes to generate optical-path differences in the respective gaps between the pairs of electrodes.

9. A light-waveform measuring device comprising: gate-pulse-light generating means; measurement-light generating means; and light-detecting means for detecting measurement light,
wherein both of gate pulse light and measurement light are coherent lights, the measurement light is coherent light having a wavelength longer than that of 100 THz, the measurement light and the gate pulse light are directed to the light-detecting means to generate carriers therein, a physical quantity based on the carriers is measured and an electric field of the measurement light is measured, in real time, on the basis of the physical quantity.

10. A light-waveform measuring method comprising: gate-pulse-light generating means; measurement-light generating means; and light-detecting means for detecting measurement light,
both of gate pulse light and measurement light being coherent lights, the measurement light being a coherent electromagnetic wave or coherent visible light having a wavelength smaller than those of terahertz electromagnetic waves, the gate pulse light having a pulse width smaller than a period of the measurement light, the gate pulse light being directed to the light-detecting means to generate carriers therein, a physical quantity based on the carriers being measured, and an electric field of the measurement light being measured on the basis of the physical quantity, wherein
the light-detecting means includes plural pairs of electrodes, wherein there are provided different optical-path differences for the gate pulse light directed to the gaps between the respective pairs of electrodes, and the physical quantities generated in the respective gaps between the electrodes are acquired as sampling data, with the plural optical-path differences and with a single irradiation of the gate pulse light to measure the electric field of the measurement light.

11. The light waveform measuring method according to claim 10, wherein the gate pulse light is directed to the plural pairs of electrodes diagonally with respect to the surfaces of detection electrodes to generate optical-path differences in the respective gaps between the pairs of electrodes.

12. A complex-refractive-index measuring device comprising: gate-pulse-light generating means; measurement-light generating means; light-detecting means for detecting measurement light; and data processing means,
both of gate pulse light and measurement light being coherent lights, the gate pulse light having a pulse width smaller than a period of the measurement light, the gate pulse light being directed to the light-detecting means to generate carriers therein, a physical quantity based on the carriers being measured, and an electric field of the measurement light being measured on the basis of the physical quantity, wherein the data processing means includes a data holding unit for holding the measurement data, and holds measurement data of an electric field of the measurement light which does not pass through a sample and an electric field of the measurement light having passed through the sample and makes a comparison between the electric field of the measurement light which does not pass through the sample and the electric field of the measurement light having passed through the sample to obtain a complex refractive index of the sample.

13. The complex-refractive-index measuring device according to claim 12, wherein the data processing device includes Fourier transform means, and obtains waveforms of the electric fields of the measurement light which does not pass through the sample and the measurement light having passed through the sample, applies a Fourier transform to these waveforms and obtains the complex refractive index on the basis of the Fourier transforms.

14. The complex-refractive-index measuring device according to claim 13, wherein the measurement light is light with a frequency of 0.1 THz to 67 THz.

15. The complex-refractive-index measuring device according to claim 12, wherein the measurement light is light with a frequency of 0.1 THz to 67 THz.

16. The complex-refractive-index measuring device according to any one of claims 12, wherein the light-detecting means includes plural pairs of electrodes, there are different optical-path differences for the gate pulse light directed to the gaps between the respective pairs of electrodes, and the physical quantities generated in the respective gaps between the electrodes are acquired as sampling data, with the plural optical-path differences and with a single irradiation of the gate pulse light to measure the electric field of the measurement light.

17. The complex-refractive-index measuring device according to claim 16, wherein the gate pulse light is directed to the plural pairs of electrodes diagonally with respect to the surfaces of detection electrodes to generate optical-path differences in the respective gaps between the pairs of electrodes.

18. A complex-refractive-index measuring method comprising: gate-pulse-light generating means; measurement-light generating means; light-detecting means for detecting measurement light; and data processing means, both of gate pulse light and measurement light being coherent lights, the gate pulse light having a pulse width smaller than a period of the measurement light, the gate pulse light being directed to the light-detecting means to generate carriers therein, a physical quantity based on the carriers being measured, and an electric field of the measurement light being measured on the basis of the physical quantity, wherein the data processing means includes a data holding unit for holding the measurement data, and holds measurement data of an electric field of the measurement light which does not pass through a sample and an electric field of the measurement light having passed through the sample and makes a comparison between the electric field of the measurement light which does not pass through the sample and the electric field of the measurement light having passed through the sample to measure a complex refractive index of the sample.

19. The complex-refractive-index measuring method according to claim 18, wherein the data processing device includes Fourier transform means, and obtains waveforms of the electric fields of the measurement light which does not pass through the sample and the measurement light having passed through the sample, applies a Fourier transform to these waveforms, and obtains the complex refractive index on the basis of the Fourier transforms.

20. The complex-refractive-index measuring method according to claim 19, wherein the light-detecting means includes plural pairs of electrodes, there are provided different optical-path differences for the gate pulse light directed to the gaps between the respective pairs of electrodes, and the physical quantities generated in the respective gaps between the electrodes are acquired as sampling data, with the plural optical-path differences and with a single irradiation of the gate pulse light, to measure the electric field of the measurement light.

21. The complex-refractive-index measuring method according to claim 20, wherein the gate pulse light is directed to the plural pairs of electrodes diagonally with respect to the surfaces of detection electrodes to generate optical-path differences in the respective gaps between the pairs of electrodes.

22. The complex-refractive-index measuring method according to claim 18, wherein the light-detecting means includes plural pairs of electrodes, there are provided different optical-path differences for the gate pulse light directed to the gaps between the respective pairs of electrodes, and the physical quantities generated in the respective gaps between the electrodes are acquired as sampling data, with the plural optical-path differences and with a single irradiation of the gate pulse light, to measure the electric field of the measurement light.

23. The complex-refractive-index measuring method according to claim 22, wherein the gate pulse light is directed to the plural pairs of electrodes diagonally with respect to the surfaces of detection electrodes to generate optical-path differences in the respective gaps between the pairs of electrodes.

24. A computer readable program code disposed on a non-transitory computer readable medium for light-waveform measuring comprising:

a computer readable program code disposed on a non-transitory computer readable medium, configured for inputting data obtained by applying a Fourier transform to measurement data of an electric field of a waveform of measurement light having a wavelength longer than that of 100 THz; and a computer readable program code disposed on a non-transtory computer readable medium, configured for obtaining a complex refractive index on the basis of the Fourier transforms of the measurement light which does not pass through a sample and the measurement light which has passed through the sample;

wherein the complex refractive index of the sample is obtained by a computer, on the basis of the measurement data of the electric-field waveform of the measurement light.

* * * * *

UNITED STATES PATENT AND TRADEMARK OFFICE
CERTIFICATE OF CORRECTION

PATENT NO. : 7,787,122 B2
APPLICATION NO. : 10/561280
DATED : August 31, 2010
INVENTOR(S) : Shingo Saito, Masaru Iida and Masaaki Ashida It is certified that error appears in the above-identified patent and that said Letters Patent is hereby corrected as shown below:

Column 21, line 51, "claim 1" should be changed to --claim 3--.

Column 21, line 54, "claim 1" should be changed to --claim 4--.

Column 23, line 29, "according to any one of claims 12" should be changed to --according to claim 12--.

Column 24, line 38, "claim 22" should be changed to --claim 20--.

Signed and Sealed this

Thirtieth Day of November, 2010

David J. Kappos
*Director of the United States Patent and Trademark Office*